United States Patent
Nguyen et al.

(10) Patent No.: US 10,874,786 B2
(45) Date of Patent: Dec. 29, 2020

(54) IMPLANTABLE DIALYSIS DEVICE

(71) Applicant: Nephrodite LLC, Atlanta, GA (US)

(72) Inventors: Hiep Nguyen, Chandler, AZ (US); Nikhil Shah, Atlanta, GA (US); Julie Wilderman, Atlanta, GA (US)

(73) Assignee: NEPHRODITE LLC, Atlanta, GA (US)

( * ) Notice: Subject to any disclaimer, the term of this patent is extended or adjusted under 35 U.S.C. 154(b) by 388 days.

(21) Appl. No.: 15/992,595

(22) Filed: May 30, 2018

(65) Prior Publication Data
US 2018/0344913 A1    Dec. 6, 2018

Related U.S. Application Data

(60) Provisional application No. 62/513,306, filed on May 31, 2017.

(51) Int. Cl.
*A61M 1/16* (2006.01)
*A61M 1/28* (2006.01)

(52) U.S. Cl.
CPC ........ *A61M 1/1621* (2014.02); *A61M 1/1601* (2014.02); *A61M 1/1623* (2014.02); *A61M 1/1633* (2014.02); *A61M 1/1678* (2013.01); *A61M 1/285* (2013.01); *A61M 2205/04* (2013.01)

(58) Field of Classification Search
CPC .... A61M 1/1678; A61M 1/16; A61M 1/1621; A61M 1/1623; A61M 1/1633; A61M 2205/04
See application file for complete search history.

(56) References Cited

U.S. PATENT DOCUMENTS

| | | | | |
|---|---|---|---|---|
| 4,354,933 A | * | 10/1982 | Lester | A61M 1/1678 210/257.2 |
| 4,765,907 A | * | 8/1988 | Scott | A61M 1/1696 210/321.78 |
| 4,769,037 A | * | 9/1988 | Midcalf | A61M 1/1678 604/6.09 |
| 5,092,886 A | * | 3/1992 | Dobos-Hardy | A61F 2/022 623/23.65 |
| 5,902,336 A | * | 5/1999 | Mishkin | A61F 2/064 604/27 |
| 2002/0123712 A1 | * | 9/2002 | Gorsuch | A61M 1/28 604/6.04 |

(Continued)

*Primary Examiner* — Leslie R Deak
(74) *Attorney, Agent, or Firm* — Locke Lord LLP; Tim Tingkang Xia, Esq.

(57) ABSTRACT

A dialysis device implantable in a patient for dialysis includes a filtration unit. The filtration unit includes at least one dialysis chamber for containing and/or circulating dialysate; and at least one blood chamber for containing and/or circulating blood of the patient, disposed on at least one dialysis chamber and being in communication with the at least one dialysis chamber. Each of the at least one dialysis chamber and the at least one blood chamber comprise at least one inlet for circulating fluid into and/or out of the at least one dialysis chamber and the at least one blood chamber. The at least one dialysis chamber and the at least one blood chamber are configured such that the blood in the at least one blood chamber and the dialysate in the at least one dialysis chamber operably interact with each other for dialysis.

32 Claims, 28 Drawing Sheets

(56) References Cited

U.S. PATENT DOCUMENTS

| | | | |
|---|---|---|---|
| 2006/0036332 A1* | 2/2006 | Jennings | A61M 1/1682 |
| | | | 623/23.65 |
| 2009/0234266 A1* | 9/2009 | Solomon | B01D 61/145 |
| | | | 604/6.09 |
| 2017/0258977 A1* | 9/2017 | Miki | B01D 63/087 |
| 2018/0353672 A1* | 12/2018 | Ahmadi | A61M 1/3482 |
| 2019/0232232 A1* | 8/2019 | Mendonca | A61M 1/34 |
| 2020/0114058 A1* | 4/2020 | Roy | A61M 1/1621 |

\* cited by examiner

IMPLANTABLE DIALYSIS DEVICE

CROSS-REFERENCE TO RELATED PATENT APPLICATION

This application claims priority to and the benefit of, pursuant to 35 U.S.C. § 119(e), U.S. Provisional Patent Application Ser. No. 62/513,306, filed May 31, 2017, which is incorporated herein in its entirety by reference.

FIELD OF THE INVENTION

This invention relates generally to dialysis, and more particularly to an implantable dialysis including a filtration unit with at least one blood chamber and at least one dialysis chambers.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

The human kidney serves an essential function to maintain the body's internal balance of fluid and minerals by removing harmful toxins and excess water. However, the prevalence of Chronic Kidney Disease (CKD) and End-Stage Renal Disease (ESRD) in the United States is increasing. According to recent estimates, more than 35 million Americans have been diagnosed with CKD. Patients with CKD have permanent kidney damage, although their kidneys may still function sufficiently to sustain life. However, if renal (i.e., kidney) capacity worsens, CKD may lead to total kidney failure, also known as ESRD. Patients in ERSD have less than 10-15% renal function compared to non-diseased individuals. More precisely, ESRD occurs when renal function is less than 15 ml/min./1.73 m$^2$. There were over 620,136 cases of ESRD in the United States in 2014 alone. Treatment for ESRD requires renal replacement therapy, which may take one of the following forms: renal transplantation or dialysis, primarily hemodialysis (HD) or peritoneal dialysis (PD).

Renal replacement, while the gold standard, is an intervention largely limited by the availability of donated organs. For example in 2008, the overall incidence of renal transplantation for the treatment of ESRD was less than 122 per million people and the prevalence was less than 644 per million people among all registries in over 30 European countries reporting to the Registry of European Renal Association-European Dialysis and Transplantation Association. Accordingly, the preferred treatment modality for ESRD is dialysis.

Dialysis is a routinely performed treatment for ESRD patients. Of the aforementioned 620,136 patients in the United States suffering from ESRD, approximately 350,000 are on dialysis, of which 93% are on hemodialysis—and, only 1% perform home hemodialysis. (Hemodialysis, as detailed later in this section, is a process that uses a man-made membrane, a dialyzer, to remove waste and extra water in the blood.) According to a 2010 U.S. Renal Data System (USRDS) Annual Report, the death rate for patients with ESRD was more than 20% within the first two years on dialysis, and the adjusted all-cause mortality rate was 6.4 to 7.8 times higher in dialysis patients than in the general population. While itself fatal, ESRD may also lead to other highly morbid health conditions such as chronic high blood pressure, hypertension, or heart disease. In 2008, costs for ESRD in the U.S. exceeded $26 billion, of which hemodialysis accounted for more than $19 billion. According to the United States Renal Data System, there are more 57,000 ESRD patients in France, 271,000 in Japan, and 44,000 in Spain.

Dialysis is a process to remove waste and excess water from a patient's blood, recapitulating normal kidney function. It works on the patient's vascular space, which constitutes nearly 8% of the total fluid volume in the human body. Dialysis induces changes in a small body compartment that then extend to changes inside cells (i.e., the intracellular environment), between cells (i.e., the extracellular environment), and on body tissues. Goals of dialysis include clearance (i.e., removal) of toxins and other substances from the blood and fluid elimination (i.e., ultrafiltration).

Dialysis operates based on the principles of diffusion and ultrafiltration. Diffusion is a property of molecules dissolved in water, whereby molecules move from an area where more dissolved molecules are present (high concentration) to an area where fewer are present (low concentration), or down a concentration gradient. In dialysis, a semipermeable membrane, or a membrane with microscopic holes of various sizes or pores (that may, for example, be 7.3 to 37.5 kDa in diameter), separates blood with dissolved water and toxins on one side from a cleansing solution known as dialysate on the other. Smaller dissolved substances in the blood, like water and certain toxins, pass through the membrane, while preventing passage of larger red blood cells and protein. Blood or dialysate concentration as well as properties of the semi-permeable membrane may affect the rate of diffusion. Further, smaller molecules and those of certain electric charge (i.e., a property of all matter that gives rise to electric interactions with other matter) may diffuse more quickly than larger or differently charged ones. Ultrafiltration is a process where pressure gradients lead to the movement of molecules dissolved in water through a semi-permeable membrane. In dialysis, the pressure on the dialysate side is lower, and water dissolved in the blood moves from the higher pressured blood to the lower pressured dialysate across the semipermeable membrane.

Two dialysis methods including hemodialysis and peritoneal dialysis cleanse the patient's blood in different ways. First, in hemodialysis, the patient's vascular system is accessed at an access point by one of three methods. In the first, a medical professional inserts a catheter, a tubular medical device, into a major artery. This procedure, however, introduces risk of infection and is not used for permanent access. Alternatively, a surgeon may surgically connect an artery and a vein, forming an arteriovenuous fistula. The pressure inside the vein increases, causing the walls of the vein to strengthen so that the vein may receive needles in hemodialysis for many years. Three to four months are required for the fistula to heal before it may be used for HD. Finally, a plastic tube may be surgically placed under a patient's skin in his or her arm in a U-shape loop, joining the radial artery to a nearby vein in a procedure called an arteriorvenuous graft. While such a graft requires overnight hospitalization and three weeks to heal before use in HD, it does not last as long as an arteriovenuous fistula as an access point.

Once vascular access is achieved, the patient's blood is pumped from the access point through surgical tubing and into a special machine that includes a dialyzer. The dialyzer is composed of thousands of cylindrical hollow fiber bundles, whose walls are composed of a semi-permeable membrane, fixed in a compound and placed into a shell with several openings that communicate with each end of the hollow fiber bundles. Membrane properties may be altered to provide selective clearance of certain molecules. Blood flows through the machine dialyzer into one or more openings of the dialyzer and then circulates through the bundles of hollow fibers, while dialysate is pumped through the space surrounding the fibers. The dialyzer filters the blood like one's kidney, removing waste particles and excess fluid, while other important parts of the blood like protein and red blood cells remain in the blood. Once cleansed, the blood flows out of the machine and back into the patient into a vein in the same arm.

HD typically occurs in a dialysis center, which requires equipment, staff, and a mode of transportation to the center. Patients undergoing HD must remain within reasonable distance of a dialysis center, and the costs for center staffing are high. The HD procedure is time-limited to three-hour sessions. Patients undergoing HD face serious risks, such as: infection due to the exposure of the vascular access point; potentially life-threatening blood clots (known as thrombi); and, dialysis disequilibrium syndrome, which is the occurrence of neurologic symptoms like convulsions, nausea and vomiting as well as brain swelling, related to the rapid removal of waste occurring on HD. While HD allows for significant clearance of small molecules, the treatment commonly causes low blood pressure, or intradialytic hypotension, in 5 to 30 percent of all patients due to the rapid removal of fluids.

Second, in PD, a soft plastic surgical tube known as a peritoneal catheter is surgically inserted into the patient's peritoneum, a two-layered tissue membrane containing blood vessels that lines the abdominal cavity and covers the abdominal organs. One end of the catheter protrudes from the abdomen and serves as the access point. (Peritoneal dialysis treatment may only be performed following recovery from catheterization.) Dialysate fluid, generally with high glucose concentration, is infused through the peritoneal catheter access point into the patient's abdomen and left to dwell. Diffusion drives clearance of toxins as blood passes through abdominal blood vessels in the peritoneal membrane. However, the amount of cleansing is highly variable, and it may relate to the dialysate concentration. PD requires several weeks of training, active patient participation, equipment, space for supplies including large volumes of dialysate, and a power source. Complications may include bowel or bladder perforation, damage to other organs such as fallopian tubes, and inflammation of the peritoneum, or peritonitis, which leads to peritoneal scarring.

There are many limitations to these and other dialysis regimes. A typical patient HD undergoes three dialysis treatments per week, each for approximately 3-4 hours, allowing for a total treatment time of 12 hours per week, compared to the 168 hours per week of blood cleansing in those with normal renal function. PD is less efficient than HD; consequently, patients on PD typically undergo dialysis 12-24 hours daily, with dialysate fluid exchanges as frequently as every two hours. The fluctuations in toxic substance concentrations, due to the discontinuous nature of dialysis treatment, increases strain on the circulatory system and results in a five-year reduction in life expectancy for patients on dialysis.

Evidence shows that more frequent dialysis leads to a decrease in the morbidity associated with ESRD. As a result, use of home dialysis is a priority, especially to reduce the high care costs associated with ESRD. Thus, there is need for an implantable dialysis unit that combines the benefits of HD, including better clearance and maintenance of homeostasis, with the benefits of PD, including ease of use, portability, low cost, and more gradual changes to fluid and electrolyte balance—all of which will improve the quality of life for patients living with ESRD.

SUMMARY OF THE INVENTION

In one aspect, the invention relates to a dialysis device implantable in a patient for dialysis comprising a filtration unit. In one embodiment, the filtration unit includes a top dialysis chamber and a bottom dialysis chamber for containing and/or circulating dialysate; and a blood chamber for containing and/or circulating blood of the patient, disposed between the top dialysis chamber and the bottom dialysis chamber and being in communication with the top dialysis chamber and the bottom dialysis chamber, respectively. Each of the top dialysis chamber, the bottom dialysis chamber and the blood chamber comprises at least one inlet for circulating fluid into and/or out of each of the top dialysis chamber, the bottom dialysis chamber and the blood chamber. The top dialysis chamber, the bottom dialysis chamber and the blood chamber are configured such that the blood in the blood chamber and the dialysate in the top dialysis chamber and the bottom dialysis chamber operably interact with each other for dialysis.

In one embodiment, the filtration unit further comprises first and second ultrafiltration membranes, wherein the first ultrafiltration membrane is disposed between the top dialysis chamber and the blood chamber and the second ultrafiltration membrane is disposed between the blood chamber and the bottom dialysis chamber such that the blood contained in the blood chamber is in contact with surfaces of the first and second ultrafiltration membranes that face the blood chamber, the dialysate fluid contained in the top dialysis chamber is in contact with a surface of the first ultrafiltration membrane that face the top dialysis chamber, and the dialysate fluid contained in the bottom dialysis chamber is in contact with a surface of the second ultrafiltration membrane that face the bottom dialysis chamber.

In one embodiment, the filtration unit further comprises first and second diaphragms adapted to support the first and second ultrafiltration membranes, respectively, and formed of a flexible inert material that allows the blood chamber to fill during expansion or to expel during contraction, while having opposite expansion or contraction effect on the top and bottom dialysis chambers.

In one embodiment, each ultrafiltration membrane is a porous membrane having pores that permit molecules to travel between the blood chamber and the top dialysis chamber, and between the blood chamber and the bottom dialysis chamber, whereby substances in the blood to be removed from the blood are passable from the blood in the blood chamber to the dialysate in the top dialysis chamber and the bottom dialysis chamber, or substances in the dialysate to be added into the blood are passable from the dialysate in the top dialysis chamber and the bottom dialysis chamber into the blood chamber.

In one embodiment, each ultrafiltration membrane is formed of electrospun fleece, or nanofibers of a polymer or a polymer composite material.

In one embodiment, each ultrafiltration membrane is formed of polyurethane.

In one embodiment, the pores of each ultrafiltration membrane are less than about 30 kDa in diameter.

In one embodiment, each ultrafiltration membrane is further adapted as a pressure barrier separating fluid volumes contained in the top dialysis chamber and/or the bottom dialysis chamber from that of the blood chamber.

In one embodiment, the at least inlet of the blood chamber is operably connected to a vascular system of the patient, the at least one inlet of the top dialysis chamber and/or the bottom dialysis chamber are operably connected to a dialysate reservoir, so that blood of the patient is flowable into and/or out of the blood chamber, the dialysate in the dialysate reservoir is flowable into and/or out of the top dialysis chamber and/or the bottom dialysis chamber, whereby unwanted substances of the blood in the blood chamber are exchangeable with the dialysate in the top dialysis chamber and/or the bottom dialysis chamber as the blood flows into and/or out of the blood chamber.

In one embodiment, the at least inlet of the blood chamber comprises an inlet and an outlet each having a valve configured such that when the blood chamber fills with fresh or uncleansed blood, the valve of the inlet is opened, while the valve of the outlet is closed, and when the blood chamber expels the purified blood, the valve of the outlet is opened, while the valve of the inlet is closed.

In one embodiment, the filtration unit further comprises a top housing, a bottom housing and a middle housing sealingly connected between the top housing and the bottom housing, wherein the top housing, the bottom housing and the middle housing house the top dialysis chamber, the bottom dialysis chamber and the blood chamber, respectively.

In one embodiment, each of the top housing and the bottom housing have an opening that provides a means to sealingly affix an outer membrane to each of the top housing and the bottom housing.

In one embodiment, the middle housing has at least an incompressible portion at the at least one inlet of the blood chamber for enhancing flow of the blood into and/or out of the blood chamber.

In one embodiment, the dialysis device further includes at least one pump coupled to at least one of the top dialysis chamber and the bottom dialysis chamber for conveying the dialysate to and/or from the top dialysis chamber and the bottom dialysis chamber.

In one embodiment, the at least one pump is further coupled to an internal dialysate reservoir and/or an external dialysate reservoir.

In one embodiment, the at least one pump is positioned between the top and/or bottom dialysis chambers and the internal or external dialysate reservoir.

In one embodiment, the at least one pump is attachable either fixedly within the body of the patient or removably outside the patient.

In one embodiment, the at least one pump is fixedly attachable to at least one of the top dialysis chamber and the bottom dialysis chamber.

In one embodiment, the at least one pump is programmed to alternatively cause the top dialysis chamber and the bottom dialysis chamber to pump and expel the dialysate in a cycle of pre-determined periodicity, thereby causing the blood chamber to alternately fill with and expel the blood for the dialysis.

In one embodiment, the at least one pump is further programmed to periodically pump a larger dialysate volume into the top dialysis chamber and the bottom dialysis chamber, thereby resulting in a higher pressure in the top dialysis chamber and the bottom dialysis chamber than in the blood chamber.

In another aspect, the invention relates to a dialysis device implantable in a patient for dialysis comprising a filtration unit. In one embodiment, the filtration unit includes at least one dialysis chamber for containing and/or circulating dialysate; and at least one blood chamber for containing and/or circulating blood of the patient, disposed on at least one dialysis chamber and being in communication with the at least one dialysis chamber. Each of the at least one dialysis chamber and the at least one blood chamber comprise at least one inlet for circulating fluid into and/or out of the at least one dialysis chamber and the at least one blood chamber. The at least one dialysis chamber and the at least one blood chamber are configured such that the blood in the at least one blood chamber and the dialysate in the at least one dialysis chamber operably interact with each other for dialysis.

In one embodiment, at least one dialysis chamber comprises two or more dialysis chambers, and the at least one blood chamber comprises two or more are blood chambers, and wherein the two or more dialysis chambers and the two or more are blood chambers are alternatively stacked on one another.

In one embodiment, the filtration unit further comprises at least one ultrafiltration membrane disposed between the at least one dialysis chamber and the at least one blood chamber such that the blood contained in the blood chamber is in contact with one surface of the at least one ultrafiltration membrane that face the blood chamber, the dialysate fluid contained in the at least one dialysis chamber is in contact with another surface of the at least one ultrafiltration membrane that face the at least one dialysis chamber.

In one embodiment, the filtration unit further comprises at least one diaphragm adapted to support the at least one ultrafiltration membrane, and formed of a flexible inert material that allows the at least one blood chamber to fill during expansion or to expel during contraction, while having opposite expansion or contraction effect on the at least one dialysis chamber.

In one embodiment, the at least one ultrafiltration membrane is a porous membrane having pores that permit molecules to travel between the at least one blood chamber and the at least one dialysis chamber, whereby substances in the blood to be removed from the blood are passable from the blood in the at least one blood chamber to the dialysate in the at least one dialysis chamber, or substances in the dialysate to be added into the blood are passable from the dialysate in the at least one dialysis chamber into the at least one blood chamber.

In one embodiment, the at least one ultrafiltration membrane is formed of electrospun fleece, or nanofibers of a polymer or a polymer composite material.

In one embodiment, the at least one ultrafiltration membrane is further adapted as a pressure barrier separating fluid volumes contained in the at least one dialysis chamber from that of the at least one blood chamber.

In one embodiment, the at least inlet of the at least one blood chamber is operably connected to a vascular system of the patient, the at least one inlet of the at least one dialysis chamber is operably connected to a dialysate reservoir, so that blood of the patient is flowable into and/or out of the at least one blood chamber, the dialysate in the dialysate reservoir is flowable into and/or out of the at least one dialysis chamber, whereby unwanted substances of the blood in the at least one blood chamber are exchangeable with the dialysate in the at least one dialysis chamber as the blood flows into and/or out of the at least one blood chamber.

In one embodiment, the at least inlet of the at least one blood chamber comprises an inlet and an outlet each having a valve configured such that when the at least one blood chamber fills with fresh or uncleansed blood, the valve of the inlet is opened, while the valve of the outlet is closed, and when the at least one blood chamber expels the purified blood, the valve of the outlet is opened, while the valve of the inlet is closed.

In one embodiment, the dialysis device further includes at least one pump coupled to the at least one dialysis chamber for conveying the dialysate to and/or from the at least one dialysis chamber.

In one embodiment, the at least one pump is further coupled to an internal dialysate reservoir and/or an external dialysate reservoir.

In one embodiment, the at least one pump is programmed to alternatively cause the at least one dialysis chamber to pump and expel the dialysate in a cycle of pre-determined periodicity, thereby causing the at least one blood chamber to alternately fill with and expel the blood for the dialysis.

In one embodiment, the at least one pump is further programmed to periodically pump a larger dialysate volume into the at least one dialysis chamber, thereby resulting in a higher pressure in the at least one dialysis chamber than in the at least one blood chamber.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

FIGS. 5-29 show a process of forming an elastomeric diaphragm and thermally bonding it to a dialysis membrane according to one embodiment of the present invention, wherein FIG. 5 shows about 2 grams Chronoflex AL 75A pellets placed on 0.8 mm thick silicone sheet inside of 0.3 mm thick steel spacer ring;

FIG. 6 shows about 0.8 mm thick silicone sheet placed on top of configuration shown in FIG. 5;

FIG. 7 shows an assembly placed between two heated platens on Fluidic Tools VTP-50;

FIG. 8 shows an application of heat and pressure to assembly described in FIG. 2;

FIG. 9 shows the end of heat and pressure process;

FIG. 10 shows an assembly placed on and then between thermally conductive metal platens;

FIG. 11 shows the assembly after cooling;

FIG. 12 shows the formed silicone ring is removed from the spacer ring;

FIG. 13 shows an elastomeric film after forming;

FIG. 14 shows a template placed onto elastomeric film and cut to defined diameter;

FIG. 15 shows a cut elastomeric film;

FIG. 16 shows punching a hole into the cut elastomeric film;

FIG. 17 shows clamping the cut elastomeric film between a frame and support;

FIG. 18 shows placing a boss onto the clamped elastomeric film;

FIG. 19 shows driving the boss into clamped elastomeric film;

FIG. 20 shows placing the clamped elastomeric film between heated platens;

FIG. 21 shows removing the boss from shaped film;

FIG. 22 shows boss, clamping frame and shaped elastomeric film resting on rim of aluminum cavity;

FIG. 23 shows a shaped elastomer;

FIG. 24 shows an assembly of dialysis membrane, shaped elastomer and silicone ring;

FIG. 25 shows an assembly placed into thermal press;

FIG. 26 shows an assembly allowed to cool to room temperature;

FIG. 27 shows removing silicone bonding ring from the dialysis membrane—elastomeric diaphragm assembly;

FIG. 28 shows the dialysis membrane thermally-bonded to elastomeric diaphragm; and FIG. 29 shows the dialysis membrane thermally-bonded to elastomeric diaphragm.

DETAILED DESCRIPTION OF THE INVENTION

Figure 1:
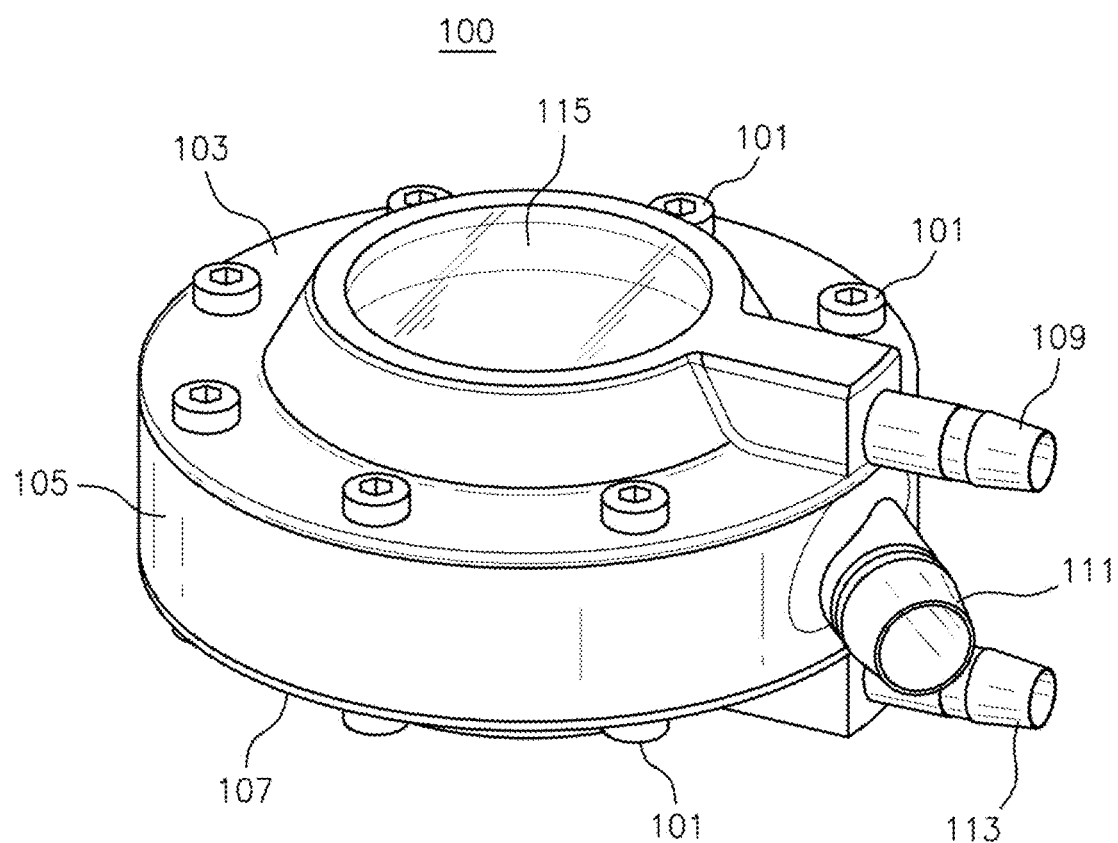
FIG. 1 is a front perspective view of a filtration unit according to one embodiment of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the phrase at least one of A, B, and C should be construed to mean a logical (A or B or C), using a non-exclusive logical OR.

As used herein, the term "inlet" refers to a port of a chamber that allows fluid to operably flow into and/or out of the chamber through the port.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The present invention relates to an implantable dialysis device, which may be totally or partially implanted in the body of a patient. The implantable dialysis device allows for continuous (24 hours per day) dialysis in or on the body of the patient. It comprises several components, including a filtration unit, an internal reservoir, an external reservoir, and a pump such as an electrohydraulic pump.

In one aspect, the invention relates to a dialysis device implantable in a patient for dialysis comprising a filtration unit. In one embodiment, the filtration unit includes a top dialysis chamber and a bottom dialysis chamber for containing and/or circulating dialysate; and a blood chamber for containing and/or circulating blood of the patient, disposed between the top dialysis chamber and the bottom dialysis chamber and being in communication with the top dialysis chamber and the bottom dialysis chamber, respectively. Each of the top dialysis chamber, the bottom dialysis chamber and the blood chamber comprises at least one inlet for circulating fluid into and/or out of each of the top dialysis chamber, the bottom dialysis chamber and the blood chamber. The top dialysis chamber, the bottom dialysis chamber and the blood chamber are configured such that the blood in the blood chamber and the dialysate in the top dialysis chamber and the bottom dialysis chamber operably interact with each other for dialysis.

In one embodiment, the filtration unit further comprises first and second ultrafiltration membranes, where the first ultrafiltration membrane is disposed between the top dialysis chamber and the blood chamber and the second ultrafiltration membrane is disposed between the blood chamber and the bottom dialysis chamber such that the blood contained in the blood chamber is in contact with surfaces of the first and second ultrafiltration membranes that face the blood chamber, the dialysate fluid contained in the top dialysis chamber is in contact with a surface of the first ultrafiltration membrane that face the top dialysis chamber, and the dialysate fluid contained in the bottom dialysis chamber is in contact with a surface of the second ultrafiltration membrane that face the bottom dialysis chamber.

In one embodiment, the filtration unit further comprises first and second diaphragms adapted to support the first and second ultrafiltration membranes, respectively, and formed of a flexible inert material that allows the blood chamber to fill during expansion or to expel during contraction, while having opposite expansion or contraction effect on the top and bottom dialysis chambers.

In one embodiment, each ultrafiltration membrane is a porous membrane having pores that permit molecules to travel between the blood chamber and the top dialysis chamber, and between the blood chamber and the bottom dialysis chamber, whereby substances in the blood to be removed from the blood are passable from the blood in the blood chamber to the dialysate in the top dialysis chamber and the bottom dialysis chamber, or substances in the dialysate to be added into the blood are passable from the dialysate in the top dialysis chamber and the bottom dialysis chamber into the blood chamber.

In one embodiment, each ultrafiltration membrane is formed of electrospun fleece, or nanofibers of a polymer or a polymer composite material.

In one embodiment, each ultrafiltration membrane is formed of polyurethane.

In one embodiment, the pores of each ultrafiltration membrane are less than about 30 kDa in diameter.

In one embodiment, each ultrafiltration membrane is further adapted as a pressure barrier separating fluid volumes contained in the top dialysis chamber and/or the bottom dialysis chamber from that of the blood chamber.

In one embodiment, the at least inlet of the blood chamber is operably connected to a vascular system of the patient, the at least one inlet of the top dialysis chamber and/or the bottom dialysis chamber are operably connected to a dialysate reservoir, so that blood of the patient is flowable into and/or out of the blood chamber, the dialysate in the dialysate reservoir is flowable into and/or out of the top dialysis chamber and/or the bottom dialysis chamber, whereby unwanted substances of the blood in the blood chamber are exchangeable with the dialysate in the top dialysis chamber and/or the bottom dialysis chamber as the blood flows into and/or out of the blood chamber.

In one embodiment, the at least inlet of the blood chamber comprises an inlet and an outlet each having a valve configured such that when the blood chamber fills with fresh or uncleansed blood, the valve of the inlet is opened, while the valve of the outlet is closed, and when the blood chamber expels the purified blood, the valve of the outlet is opened, while the valve of the inlet is closed.

In one embodiment, the filtration unit further comprises a top housing, a bottom housing and a middle housing sealingly connected between the top housing and the bottom housing, where the top housing, the bottom housing and the middle housing house the top dialysis chamber, the bottom dialysis chamber and the blood chamber, respectively.

In one embodiment, each of the top housing and the bottom housing have an opening that provides a means to sealingly affix an outer membrane to each of the top housing and the bottom housing.

In one embodiment, the middle housing has at least an incompressible portion at the at least one inlet of the blood chamber for enhancing flow of the blood into and/or out of the blood chamber.

In one embodiment, the dialysis device further includes at least one pump coupled to at least one of the top dialysis chamber and the bottom dialysis chamber for conveying the dialysate to and/or from the top dialysis chamber and the bottom dialysis chamber.

In one embodiment, the at least one pump is further coupled to an internal dialysate reservoir and/or an external dialysate reservoir.

In one embodiment, the at least one pump is positioned between the top and/or bottom dialysis chambers and the internal or external dialysate reservoir.

In one embodiment, the at least one pump is attachable either fixedly within the body of the patient or removably outside the patient.

In one embodiment, the at least one pump is fixedly attachable to at least one of the top dialysis chamber and the bottom dialysis chamber.

In one embodiment, the at least one pump is programmed to alternatively cause the top dialysis chamber and the bottom dialysis chamber to pump and expel the dialysate in a cycle of pre-determined periodicity, thereby causing the blood chamber to alternately fill with and expel the blood for the dialysis.

In one embodiment, the at least one pump is further programmed to periodically pump a larger dialysate volume into the top dialysis chamber and the bottom dialysis chamber, thereby resulting in a higher pressure in the top dialysis chamber and the bottom dialysis chamber than in the blood chamber.

In another aspect, the invention relates to a dialysis device implantable in a patient for dialysis comprising a filtration unit. In one embodiment, the filtration unit includes at least one dialysis chamber for containing and/or circulating dialysate; and at least one blood chamber for containing and/or circulating blood of the patient, disposed on at least one dialysis chamber and being in communication with the at least one dialysis chamber. Each of the at least one dialysis chamber and the at least one blood chamber comprise at least one inlet for circulating fluid into and/or out of the at least one dialysis chamber and the at least one blood chamber. The at least one dialysis chamber and the at least one blood chamber are configured such that the blood in the at least one blood chamber and the dialysate in the at least one dialysis chamber operably interact with each other for dialysis.

In one embodiment, at least one dialysis chamber comprises two or more dialysis chambers, and the at least one blood chamber comprises two or more are blood chambers, and where the two or more dialysis chambers and the two or more are blood chambers are alternatively stacked on one another.

In one embodiment, the filtration unit further comprises at least one ultrafiltration membrane disposed between the at least one dialysis chamber and the at least one blood chamber such that the blood contained in the blood chamber is in contact with one surface of the at least one ultrafiltration membrane that face the blood chamber, the dialysate fluid contained in the at least one dialysis chamber is in contact with another surface of the at least one ultrafiltration membrane that face the at least one dialysis chamber.

In one embodiment, the filtration unit further comprises at least one diaphragm adapted to support the at least one ultrafiltration membrane, and formed of a flexible inert material that allows the at least one blood chamber to fill during expansion or to expel during contraction, while having opposite expansion or contraction effect on the at least one dialysis chamber.

In one embodiment, the at least one ultrafiltration membrane is a porous membrane having pores that permit molecules to travel between the at least one blood chamber and the at least one dialysis chamber, whereby substances in the blood to be removed from the blood are passable from the blood in the at least one blood chamber to the dialysate in the at least one dialysis chamber, or substances in the dialysate to be added into the blood are passable from the dialysate in the at least one dialysis chamber into the at least one blood chamber.

In one embodiment, the at least one ultrafiltration membrane is formed of electrospun fleece, or nanofibers of a polymer or a polymer composite material.

In one embodiment, the at least one ultrafiltration membrane is further adapted as a pressure barrier separating fluid volumes contained in the at least one dialysis chamber from that of the at least one blood chamber.

In one embodiment, the at least inlet of the at least one blood chamber is operably connected to a vascular system of the patient, the at least one inlet of the at least one dialysis chamber is operably connected to a dialysate reservoir, so that blood of the patient is flowable into and/or out of the at least one blood chamber, the dialysate in the dialysate reservoir is flowable into and/or out of the at least one dialysis chamber, whereby unwanted substances of the blood in the at least one blood chamber are exchangeable with the dialysate in the at least one dialysis chamber as the blood flows into and/or out of the at least one blood chamber.

In one embodiment, the at least inlet of the at least one blood chamber comprises an inlet and an outlet each having a valve configured such that when the at least one blood chamber fills with fresh or uncleansed blood, the valve of the inlet is opened, while the valve of the outlet is closed, and when the at least one blood chamber expels the purified blood, the valve of the outlet is opened, while the valve of the inlet is closed.

In one embodiment, the dialysis device further includes at least one pump coupled to the at least one dialysis chamber for conveying the dialysate to and/or from the at least one dialysis chamber.

In one embodiment, the at least one pump is further coupled to an internal dialysate reservoir and/or an external dialysate reservoir.

In one embodiment, the at least one pump is programmed to alternatively cause the at least one dialysis chamber to pump and expel the dialysate in a cycle of pre-determined periodicity, thereby causing the at least one blood chamber to alternately fill with and expel the blood for the dialysis.

In one embodiment, the at least one pump is further programmed to periodically pump a larger dialysate volume into the at least one dialysis chamber, thereby resulting in a higher pressure in the at least one dialysis chamber than in the at least one blood chamber.

The details of exemplary embodiments of the dialysis device, particularly the filtration unit, are now described hereinafter with reference to the accompanying drawings.

Figure 2:
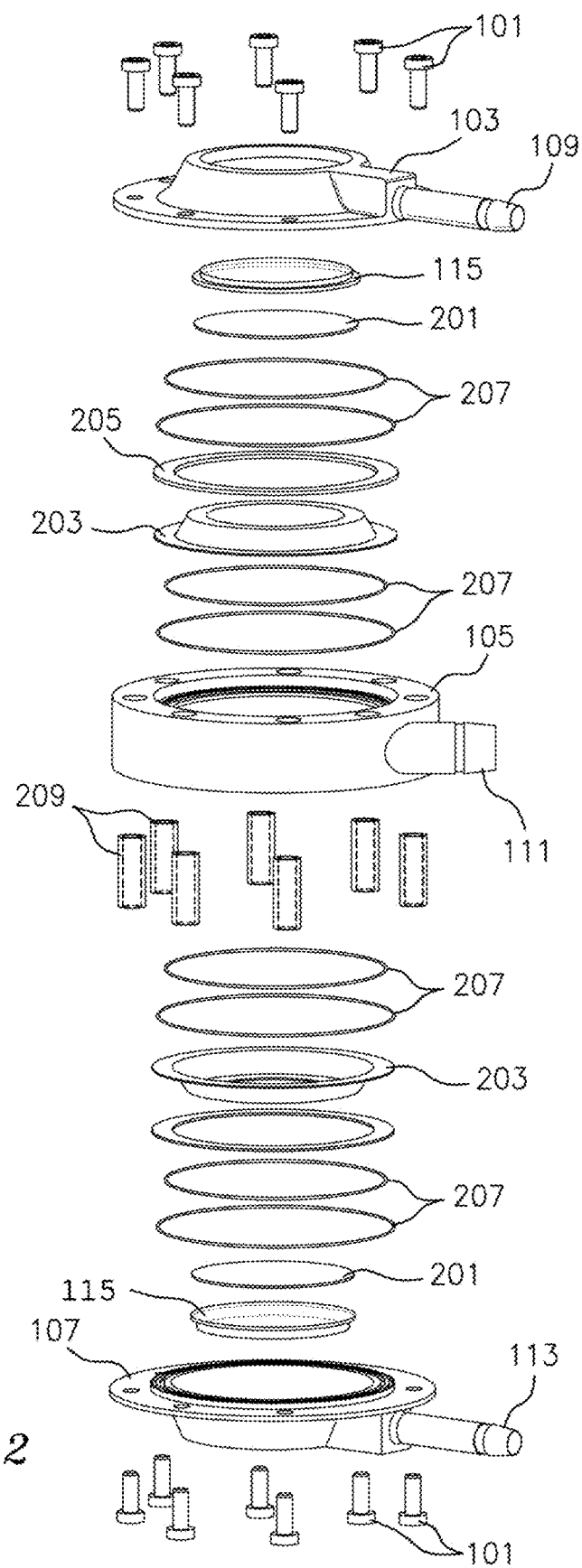
FIG. 2 is an exploded view of the filtration unit shown in FIG. 1.
Figure 3:
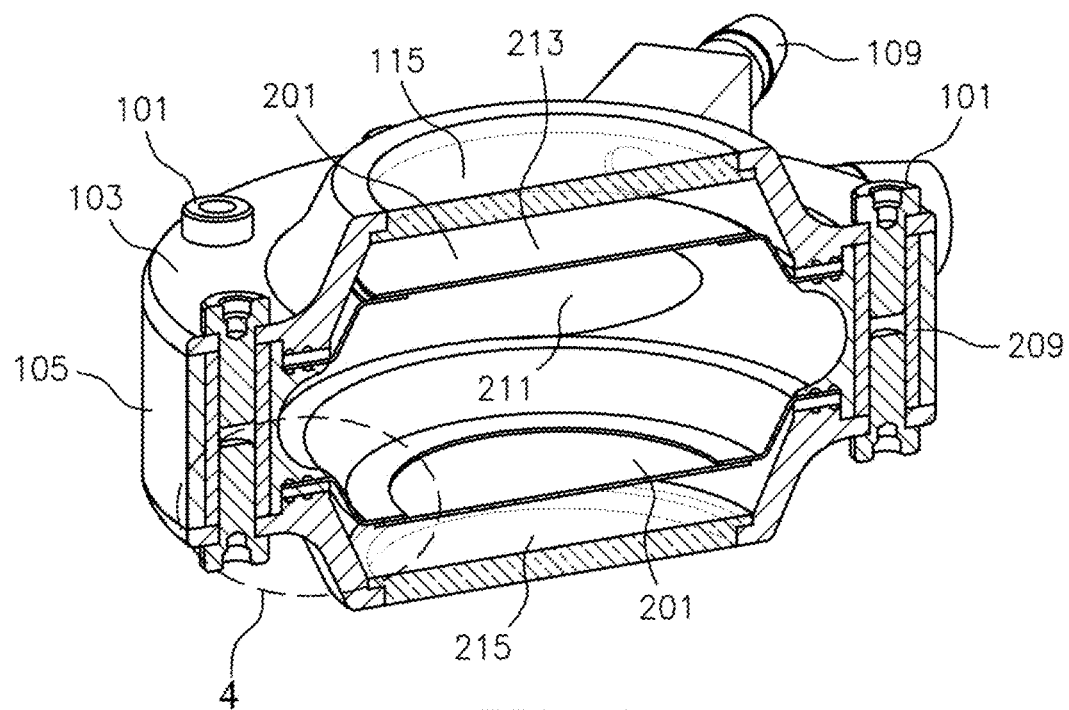
FIG. 3 is a cross-sectional view of the filtration unit shown in FIG. 1.

FIGS. 1-4 show respectively a perspective view, an exploded view, a cross-sectional view and a cross-sectional, detailed view showing the membrane mount of the filtration unit 100. The filtration unit 100, the internal reservoir (not shown), and the electrohydraulic pump (not shown) may be surgically implanted in the patient's abdomen. The internal reservoir connects to dialysis chambers of the filtration unit 100, which are illustrated in FIG. 3 in one embodiment as a top dialysis chamber 213 and a bottom dialysis chamber 215, by surgical tubing or other means. The top dialysis chamber 213 and the bottom dialysis chamber 215 of the filtration unit 100 may also attach to an external reservoir, outside the patient, by surgical tubing or other means that extends from the filtration unit 100 inside the patient to an open area on the patient to which the external reservoir may removably attach. Each of the internal reservoir and the external reservoir contains a fluid volume of a blood cleansing fluid, or dialysate. In the exemplary embodiment of the filtration unit 100, as shown in FIG. 3, the internal reservoir may be removably or permanently coupled to the first dialysis inlet 109 and/or the second dialysis inlet 113 by the aforementioned surgical tubing or other means. In a similar manner of connection, the external reservoir may alternatively be removably or permanently coupled to the first dialysis inlet 109 and/or the second dialysis inlet 113. Dialysate fluid circulates into and/or out of the first dialysis inlet 109 and also into and/or out of the top dialysis chamber 213 and also into and/or out of the second dialysis inlet 113 (shown in FIG. 2) and also into and/or out of the bottom dialysis chamber 215. A blood chamber inlet 111 may connect to the patient's vascular system through, for example, the external iliac artery by anastomosis, a surgical method to attach a graft to an artery at a 45-degree angle or a 90-degree angle. Blood thereby may flow from the patient's vascular system into and/or out of the blood chamber 211 through the blood chamber inlet 111. Blood in the blood chamber 211 then may exchange waste with the dialysate fluid in the top dialysis chamber 213 and the bottom dialysis chamber 215, respectively, as the blood is conveyed into and/or out of the blood chamber inlet 111 and, accordingly, into/or out of the blood chamber 211.

In another embodiment, the filtration unit comprises at least two dialysis chambers, the first dialysis inlet 109 and/or the second dialysis inlet 113 removably connects by means of surgical tubing to the internal reservoir, and the first dialysis inlet 109 and/or the second dialysis inlet 113 removably connects by means of surgical tubing to the external reservoir.

The filtration unit 100, depicted in FIG. 1, may have a three-chambered configuration, including, for example, a blood chamber and two dialysis chambers. As shown in the cross-sectional view of FIG. 3, a top dialysis chamber 213 may be positioned atop a blood chamber 211, and a bottom dialysis chamber 215 would be positioned below the blood chamber 211. Each diaphragm 203 supports an ultrafiltration membrane 201. By this configuration, ultrafiltration membranes 201 demarcate each side of the blood chamber 211, separating the top dialysis chamber 213 and the bottom dialysis chamber 215 from the blood chamber 211 at opposite sides, so that blood contained in the blood chamber 211, to one side of the ultrafiltration membrane 201, is in contact with the ultrafiltration membranes 201 of both of the top dialysis chamber 213 and the bottom dialysis chamber 215 that contain dialysate fluid. Other embodiments may include additional dialysis chambers 213 to increase surface area of the ultrafiltration membrane 201 and thereby increase blood contact with the ultrafiltration membranes 201 to each side of the top dialysis chamber 213 and the bottom dialysis chamber 215. Such a layered configuration of dialysis chambers and blood chambers may also apply to other embodiments of the filtration unit 100 (shown in FIG. 1), with fewer or more dialysis chambers and/or blood chambers.

In one embodiment, each of the top dialysis chamber 213 and the bottom dialysis chamber 215 may hold a fluid volume of up to about 10 mL. In another embodiment, each of the top dialysis chamber 213 and the bottom dialysis chamber 215 may hold a fluid volume greater than about 10 mL.

Still referring to FIG. 3, the ultrafiltration membranes 201 have pores, which permit molecules to travel between the blood chamber 211 and the top dialysis chamber 213 and the bottom dialysis chamber 215. Waste substances, water, or toxins in the blood to be removed, pass from the blood in the blood chamber 211 to the dialysate in the top dialysis chamber 213 and the bottom dialysis chamber 215, or other substances may pass from the dialysate in the top dialysis chamber 213 and the bottom dialysis chamber 215 into the blood chamber 211. This effect on certain constituent elements of the blood, or, as used in the art, "blood cleansing," may be achieved by means of diffusion (i.e., property of molecules dissolved in water, whereby molecules move from an area where more dissolved molecules are present to an area where fewer dissolved molecules are present) or of ultrafiltration (i.e., a pressure gradient leads to the movement of molecules dissolved in water through a semi-permeable membrane). The use of an electrohydraulic pump (not shown) may increase ultrafiltration, since the pressure gradient between the blood chamber 211 and a dialysis chamber 213 or 215 may be adjusted, as discussed further below.

The composition and structure of the ultrafiltration membrane 201 may modulate blood cleansing, namely by permitting certain sized and charged substances in the blood to pass through membrane pores to the exclusion of other substances, known as membrane "permeability."

In one embodiment of the filtration unit, as shown in FIG. 3, each ultrafiltration membrane 201 has a surface area of about 9.1 cm$^2$. The thickness of the ultrafiltration membrane 201 may range between about 30-40 Da, and it may have about 15000 fibers at a diameter of about 150 Da to achieve blood cleansing. The fibers create a mesh that determines the number of pores and consequently the permeability of the membrane. In addition, the physical properties of the fibers such as the charge of the fibers determine what molecules can be filtered through. The ultrafiltration membrane 201 may be composed of various materials, such as Satorious polyesthersulfone (a pore size of about 30 kDa). In another embodiment, the pores of the ultrafiltration membranes 201 are less than about 30 kDa in diameter, allowing molecules such as water to pass through the membrane 201. For example, waste molecules in blood smaller than about 500 Da pass from the blood chamber and through the pores of the ultrafiltration membranes and into the dialysis chambers. Waste molecules include water about 18.02 Da, sodium about 22.9 Da, and poison urea about 60.06 Da. In another embodiment, the ultrafiltration membrane 201 may be formed of electrospun fleece, a porous membrane formed of nanofibers of polymer or polymer composite material. Such an ultrafiltration membrane 201 combines the area to filter and the area for supporting mechanical movement.

In another embodiment, the ultrafiltration membrane 201 may be formed of polyurethane.

The ultrafiltration membrane 201 also serves as a pressure barrier separating, at least in part, the fluid volumes contained in the top dialysis chamber 213 and the bottom dialysis chamber 215 from that of the blood chamber 211, as shown in the cross-sectional view of FIG. 3. Since the device performs continuous dialysis in or on the body of the patient, the pump ensures the constant exchange of blood to be purified. The pump (not shown), in one embodiment, may be coupled to at least one or all dialysis chambers, for example, the top dialysis chamber 213 and/or the bottom dialysis chamber 215. Alternatively, the pump may be coupled to the internal reservoir (not shown) and/or the external reservoir (not shown).

The pump conveys dialysate to and/or from the top dialysis chamber 213 and the bottom dialysis chamber 215; however, the pump does not act upon the blood chamber 211 directly since the mechanical loads during pumping (i.e., the increases and decreases in pressure in the blood chamber) would be damaging to the blood. For example, as the pump causes the top dialysis chamber 213 to be filled with dialysate from the internal reservoir and/or the external reservoir, the ultrafiltration membrane 201 is moved toward the blood chamber 211, which adjoins the top dialysis chamber 213. The same principle may apply to direct action on the bottom dialysis chamber 215 and further indirect action on the blood chamber 211; and, this principle may also be applied to all other possible embodiments of the present invention, including a filtration unit with fewer or more dialysis and/or blood chambers and/or a filtration unit that connects to one more pumps. The action of the pump upon the top dialysis chamber 213 and the bottom dialysis chamber 215 causes the blood chamber 211 to alternately fill with and expel blood. By controlling the pump, it is possible to indirectly control the velocity and pressure at which blood from the patient's vascular system is conveyed into and out of the blood chamber 211, and, thus, exact control on the blood cleansing process.

In another embodiment, the pump may be attached fixedly to one or both of the top dialysis chamber 213 and the bottom dialysis chamber 215. In an additional embodiment, each of the top dialysis chamber 213 and the bottom dialysis chamber 215 may has one pump fixedly attached thereto.

In another embodiment, the pump may be positioned between the dialysis chamber 213 or 215 and the internal or external reservoir. The pump may attach either fixedly within the patient's body or removably outside the patient.

In an embodiment, the pump may be battery-operated and programmed to alternatively cause the dialysis chambers, shown in FIG. 3 as 213 and 215, to pump and expel dialysate fluid in a cycle of pre-determined periodicity. For example, in one embodiment, the pump causes the dialysate fluid to be pumped into and out of the top dialysis chamber 213 and the bottom dialysis chamber 215, repeating a filling and expulsion cycle where, dialysate fluid fills the top dialysis chamber 213 and the bottom dialysis chamber 215 for about 3 seconds and then is expelled for about 3 seconds from those top dialysis chamber 213 and the bottom dialysis chamber 215.

In one embodiment, the pump is powered by a power source external to the pump and the body of the patient; and, in an alternate embodiment, the pump is powered by a power source internal to the patient.

Over time, the ultrafiltration membrane 201 pores may fill with residual waste, reducing the efficiency of waste and water exchange between the blood chamber 211 and the top dialysis chamber 213 and the bottom dialysis chamber 215, as depicted in FIG. 3. In an embodiment, the pump periodically pumps a larger dialysate fluid volume into the top dialysis chamber 213 and the bottom dialysis chamber 215, which, in turn, results in a higher pressure in the top dialysis chamber 213 and the bottom dialysis chamber 215 than in the blood chamber 211. As a result, the pressure and concentration gradient reverses, forcing clogged waste out from the ultrafiltration membrane 201 pores and into the blood in the blood chamber 211. This ultrafiltration membrane cleaning cycle may be commenced, in one embodiment, automatically by a pre-programmed periodic cycle of the pump, whereby the pump causes a higher fluid volume of dialysate fluid to be conveyed into the top dialysis chamber 213 and the bottom dialysis chamber 215. In another embodiment, the patient or user may mechanically cause the pump to convey such a higher fluid volume into the top dialysis chamber 213 and the bottom dialysis chamber 215 and thereby force clogged waste from the ultrafiltration membrane 201 pores and into the blood chamber 211. The pump's action upon the dialysis chambers 211 and 213 may also apply to other embodiments of the filtration unit, whereby the filtration unit comprises more or fewer dialysis and/or blood chambers, and, accordingly, more or fewer ultrafiltration membranes.

In one embodiment, enzymatic solution comprises the larger fluid volume in the top dialysis chamber 213 and the bottom dialysis chamber 215. The enzymatic solution breaks down chemical bonds between amino acids that comprise platelets and other blood proteins that may clog pores and/or form thrombi. The external reservoir may contain the enzymatic solution so that the patient may, in another embodiment of the present invention, manually connect the external reservoir to an open area on the patient that is coupled to the device.

To prevent blood in the blood chamber 211 that has been cleansed from mixing with fresh or uncleansed blood from the patient's circulatory system, it may be possible to use a separate inlet and outlet for the blood chamber 211 with respective valves. When the blood chamber fills with fresh or uncleansed blood, a valve at the inlet can be opened, while a valve the outlet may be closed. To expel the purified blood, such an outlet valve is then opened while the inlet valve may be closed. The alternate opening and closing of the blood chamber inlets may be controlled mechanically, through, for example, a valve system with an actuator or such opening and closing of the inlets and outlets may be controlled automatically.

Alternatively, referring to FIG. 2, the blood chamber may have a common inlet and outlet, whereby blood is conveyed into and/or out of the blood chamber from the same inlet, depicted as the blood inlet as item 111. Since the device performs continuous dialysis, cleansed blood would be partially expelled through the blood inlet 111 and into the patient's vascular system. Fresh blood would then be conveyed into the blood chamber (not shown) and mix with the unexpelled cleansed blood. In such an embodiment, unpurified blood from the circulatory system may flow into the blood chamber (not shown) on systolic heartbeat and then be expelled following cleansing from the blood chamber on diastolic heartbeat, then providing space for unpurified blood to again enter the blood chamber during systole. Since blood enters and exits the blood chamber through one point, the blood chamber inlet 111, optimal flow dynamics ensure a perfect flow vortex occurs so that blood is in contact with every surface of the ultrafiltration membranes to enable maximum diffusion against the dialysate. The perfect flow vortex is a metric based on computer modeling of blood flow through the chambers that measure how uninterrupted the flow is across a membrane. If a substance passes through the pore of the membrane, it moves to the other chamber; if it does not fit through the pore then it goes along the entire membrane. Specific inlet and outlet configurations modulate substance exposure to the membrane surface to reduce continuous flow turbulence or interruption. The ability of blood to enter and exit the same inlet without recirculating means that the blood entering the blood chamber will always contain waste, thus maximizing diffusion, ultrafiltration, and accordingly blood cleansing. Optimal flow measures the amount of dead space and stagnation of molecules dissolved cycling through a volume of fluid. Stagnation causes clotting and the formation of thrombi, or blood clots, of certain clotting factors (i.e., platelets and other proteins). Ensuring the constant movement of blood is important to reduce risk of such clotting. Accordingly, the optimal flow achieved through the configuration of the blood chamber 211 shown in FIG. 2 reduces dead spaces and stagnation areas, supports prevention of thrombus formation, and improves efficiency of toxin and water clearance.

Referring now to the structure of the filtration unit, as shown in the perspective view of FIG. 1, the filtration unit 100 includes a middle housing 105 sealingly connected to both a top housing 103 and a bottom housing 107 by a plurality of fasteners 101. FIG. 3 depicts a cross-sectional view of the filtration unit 100, the top housing 103 and the bottom housing 107 contain the top dialysis chamber 213 and the bottom dialysis chamber 215, respectively, and the middle housing 105 contains the blood chamber 211. The top housing 103 and the bottom housing 107 have openings that provide a means to sealingly affix outer membranes 115 to the top housing 103 and the bottom housing 107.

The filtration unit 100, as assembled, is watertight, achieved, in part, through the use of water-resistant materials, such as polyurethane, and its assembly. The top housing 103 comprises a plurality of beveled edges that are adapted to sealingly fit a plurality of O-rings, shown as item 207 in FIG. 2, that secure the top housing 103 to the membrane mount 205. The bottom housing 107 may also comprise a plurality of beveled edges that are adapted to sealingly fit a plurality of O-rings 207 that secure the bottom housing 107 to the membrane mount 205. Similarly, the top housing 103 may also comprise a plurality of beveled edges that are adapted to sealingly fit a plurality of O-rings 207 that secure the top housing 103 to the membrane mount 205. The middle housing may also comprise a plurality of beveled edges that are adapted to sealingly fit a plurality of O-rings 207 that secure the middle housing 105 to flexible diaphragms 203. When assembled, the flexible diaphragms 203 are positioned to between the membrane mount 205 and the middle housing 105. The membrane mounts 205 are secured to the flexible diaphragms 203 by a plurality of fasteners 101 each adapted to fit in anchors 209 that secure the top housing 103 to the middle support frame 105 and that secure the middle support frame 105 to the bottom housing 107. This layered assembly by means of fasteners 101 creates a watertight seal.

In an embodiment of the filtration unit, the fasteners 101 fit into anchors 209, the latter of which fit into and traverse the perimeter of the middle housing 105. The fasteners 101 may extend from the top housing 103 and/or the bottom housing 107 midway through the anchors 209 that fit the middle housing 105. In another embodiment, fasteners may extend from the top housing 103 through the anchors 209 that fit into the middle housing 105 and into the bottom housing 107; or, fasteners may extend from the bottom housing 107 through the anchors 209 that fit the middle housing 105 and into the top housing 103.

In an embodiment, the top housing 103, the middle housing 105, and the bottom housing 107 are formed of inert materials. The fasteners 101 may also be formed of an inert material, such as surgical-grade steel. The O-rings 207 and the anchors 209 may too be made of an inert material.

In another embodiment of the filtration unit, and referring to FIG. 2, the blood chamber 211 may be housed in an incompressible middle housing 105, and the top dialysis chamber 213 and the bottom dialysis chamber 215 may be housed in the top housing 103 and the bottom housing 107, respectively. In this embodiment, the blood chamber 211 is positioned between the top dialysis chamber 213 and the bottom dialysis chamber 215. To optimize blood flow, the middle housing 105 may have an incompressible section at the blood inlet, enhancing flow of blood into and/or out of the blood chamber 211. The configuration of the housing optimizes the flow and ensures that there are no dead spaces or stagnate areas. This configuration further enables more efficient waste and water exchange at the ultrafiltration membrane 201 between blood contained in the blood chamber 211 and dialysate fluid in the top dialysis chamber 213 and the bottom dialysis chamber 215. In an embodiment, the diaphragm 203 is formed of a flexible inert material that allows the blood chamber 211 to fill during expansion and to empty during contraction, while having the opposite expansion or contraction effect on the dialysis chambers 213 and 215.

Figure 4:
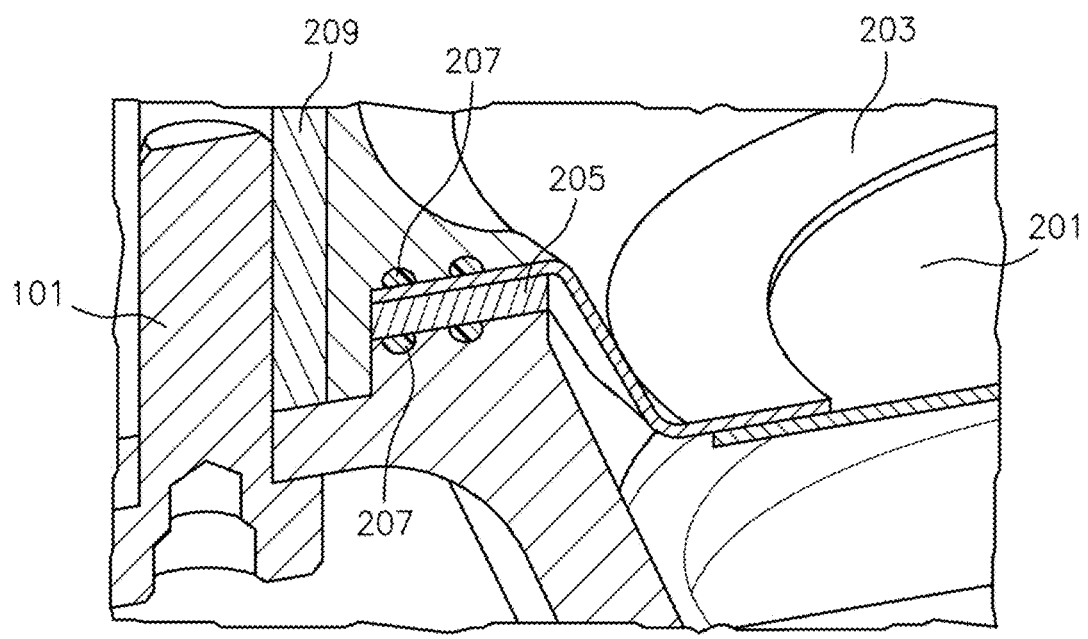
FIG. 4 is a cross-sectional, detailed view of the filtration unit shown in FIG. 1, showing the membrane mount.

Referring to FIG. 4, ultrafiltration membranes 201, situated upon a diaphragm 203, are arranged between the blood chamber 211 and the dialysis chambers, shown as item 213 and 215 of FIG. 2. A flexible membrane mount 205 is positioned between the bottom housing, shown as item 107 of FIG. 1, and the diaphragm 203. In this context, "flexible" means that the shape of the membrane mount can be changed so that at least a part of the membrane mount 205 is displaced towards the blood chamber 211 or the dialysis chamber, shown as item 215 of FIG. 3, and, as such, a compression of the blood chamber 211 may occur. The membrane mount 205 relieves dynamic stressors, caused by rapid compression and decompression, on the blood and dialysis chambers, preventing ultrafiltration membrane 201 from rupturing. The membrane mount 205 may be made from polyurethane, which may be molded by compression (about 0.3 MPa) and heat (about 205° C.) over a period of time (about 5 min.) into thin films (for example, about 300 micrometers in thickness). In another embodiment, the dialysis membranes may be thermally bonded to the membrane mount using a patterned tool with the application of heat (about 205° C.), pressure (0.3 MPa), and time (about 10 sec.). In an embodiment of the filtration unit, as shown in FIG. 1, the fibers create a mesh that determines the number of pores and consequently the permeability of the membrane. In addition, the physical properties of the fibers such as the charge of the fibers determine what molecules can be filtered through. For example, waste molecules in blood smaller than about 500 Da pass from the blood chamber and through the pores of the ultrafiltration membranes and into the dialysis chambers. Waste molecules include water about 18.02 Da, sodium about 22.9 Da, and poison urea about 60.06 Da, the device performs continuous dialysis, 24 hours per day, by two operation modes: Daytime Mode and Nighttime Mode. Nighttime mode may be activated by manual connection to the external dialysis reservoir, similar to peritoneal dialysis. This achieves more efficient and gentler blood cleansing, with decreased strain on the circulation system. During the Daytime Mode, which may last approximately 16 hours, dialysis is performed with the internal dialysis reservoir. The internal dialysis reservoir may hold a volume of approximately 500 mL of dialysate fluid. During the Nighttime Mode, which may last approximately 8 hours, the first dialysis inlet 109 and/or the second dialysis inlet 113 attach by means of a surgical tube that extends outside the patient to an external dialysis reservoir, which has a larger volume than the internal dialysis reservoir. In one embodiment, the external dialysis reservoir may hold a volume of approximately 4 L of dialysate fluid. The Daytime Mode may only remove a limited amount of waste product and water from blood provided the volume of the internal dialysis reservoir. Accordingly, the Nighttime Mode permits waste and water removal so the patient's blood may reach optimal physiological levels, which are based on the average excretion of urea and water by a human. Specifically, a normal human on a daily basis excretes approximately 1 L to about 1.5 L of fluid and about 5 g of urea. Since kidney failure hinders the ability to create, and therefore excrete, waste, the filtration unit accommodates the removal of about 1 L to about 1.5 L of water and about 5 g of urea per day to mimic healthy kidney function.

Experiments to mimic the Daytime Mode reveal the pressure of about 110 mmHg on one ultrafiltration membrane of about 30 kDa is sufficient to remove about 1.5 liters of waste over a period of about 16 hours. Similarly, the pressure of under about 100 mmHg on one such ultrafiltration membrane may extract almost 1 L of fluid. Since two ultrafiltration membranes are present in the filtration unit, a target fluid amount is obtainable even by a smaller pressure gradient. Diffusion tests on the ultrafiltration membrane of about 30 kDa show removal of about 4.00 mg of urea from a blood solution over an eight-hour period during the Nighttime Mode. This configuration enables more efficient waste and water exchange at the ultrafiltration membrane 201.

Integral to the functioning and structural integrity of the dialysis device is the joining of the dialysis membranes to the diaphragms. The diaphragms are ideally elastomeric for pre-formation flexibility and post-formation durability. The dialysis membranes must be securely attached to the elastomeric diaphragms without sealing the pores of the dialysis membrane. This may be accomplished for providing an opening in the elastomeric diaphragm over which the dialysis membrane may be secured. Since the attachment means include the use of heat and pressure, the joining must be executed carefully so as to prevent damage to the material as well as to ensure against the dialysis membrane detaching from the elastomeric diaphragm during use.

The elastomeric diaphragm may be materially sourced from polyurethane pellets. Polyurethane is useful because of its thermo-forming properties, including thermosetting attributes. One acceptable source of polyurethane is ChronoFlex AL 75A thermoplastic pellets which may be obtained from AdvanSource Biomaterials. Approximately 2 grams of these pellets are sufficient to form each diaphragm, after accounting for process discard. These pellets may be placed onto a silicone film to prevent leakage and maintain a smooth surface during heat and pressure actuated fabrication. The silicone film may be approximately 0.8 mm to enable a degree of uniform compression shielding. A first template for the diaphragm, such as a circular 0.3 mm thick steel ring may be placed around the pellets for size and thickness specificity, over which another silicone film may be placed for additional uniform compression shielding and heat and pressure control. In this instance, this first template should be at least 60 mm in diameter.

This assembly may be placed between two platens of a thermal press, such as the Fluidic Tools VTP-50, obtained from Aixtek. The platens are ideally pre-heated to about 190 degrees Celsius. After approximately five minutes of incubation, the platens are closed and approximately 0.3 MPa of pressure is then applied via the platens for approximately five minutes. The assembly may then be removed and placed between two separate thermally conductive platens to cool to room temperature. The elastomeric film may then be removed from the template.

A second template may be placed flush against the elastomeric film, the latter of which may then be cut to the dimensions of the former. In this instance, the second template is circular and approximately 61 mm in diameter. A central portion of the elastomeric film may then be cut or punched out. In this instance, a punch-out is affected using a steel die of approximately 18 mm diameter. The elastomeric film may then be placed on a three-dimensional template for thermo-shaping. The three-dimensional template may feature a top portion and a bottom portion, the bottom portion having a circumferential ridge which sloped inward and downward into a well having a flat bottom. The well may feature an incline of approximately 20 degrees. The elastomeric film may be placed on top of the circumferential ridge so that upon heating, a central portion surrounding the cut-out may drip or flex down toward the well. The formation may also occur using force-stress by means of a boss shaped like the well and extending from the top portion of the three dimensional template, so that when the top portion is pressed against the bottom portion, the elastomeric film is forced into the shape of the well by the drum. In one embodiment, the three dimensional template, which may comprise two rigid, thermally conductive halves, is placed between two heated platens of the thermal press. The platens may be heated or pre-heated to about 65 degrees Celsius and maintained at this temperature for approximately ten minutes. In this instance, the three-dimensional template halves are made of aluminum.

The elastomeric film, now a shaped elastomer, may be joined to a dialysis membrane in the following process. The dialysis membrane may be a disc of approximately 28 mm in diameter and formed out of polyethersulfone with a 30,000 molecular weight cut-off. The dialysis membrane may be placed on the internal side of the well-portion of the shaped elastomer, and an approximately 0.8 mm thick silicone ring may be placed on the opposing external side. The silicone ring should be sized proportionate or equally to the dialysis membrane, which is circular and sized to at least cover the cut-out of the shaped elastomer as well as being in a flush connection with a circumferential thickness portion around the cut-out.

The shaped elastomer, dialysis membrane, and silicone ring are then placed conformably to the bottom portion of the three-dimensional template and placed into the thermal press, the heaten platens heated to about 205 degrees Celsius. The assembly is then allowed to cool to room temperature. The silicone ring may be removed, leaving the dialysis membrane thermally-bonded to the elastomeric diaphragm.

One or more of the steps may be conflated to increase the speed of diaphragm production. For example, polyurethane pellets may be distributed within the first template and around a central column having the same thickness as the first template, thus obviating the step of cutting or punching out the central portion.

Without intent to limit the scope of the invention, examples and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Sealing a Dialysis Membrane onto a Formed Elastomeric Shape

These exemplary examples describe the use of heat and pressure to join a thermoplastic elastomeric support to a dialysis membrane without sealing the pores of the dialysis membrane.

Example 1

Forming an Elastomeric Film

Figure 5:
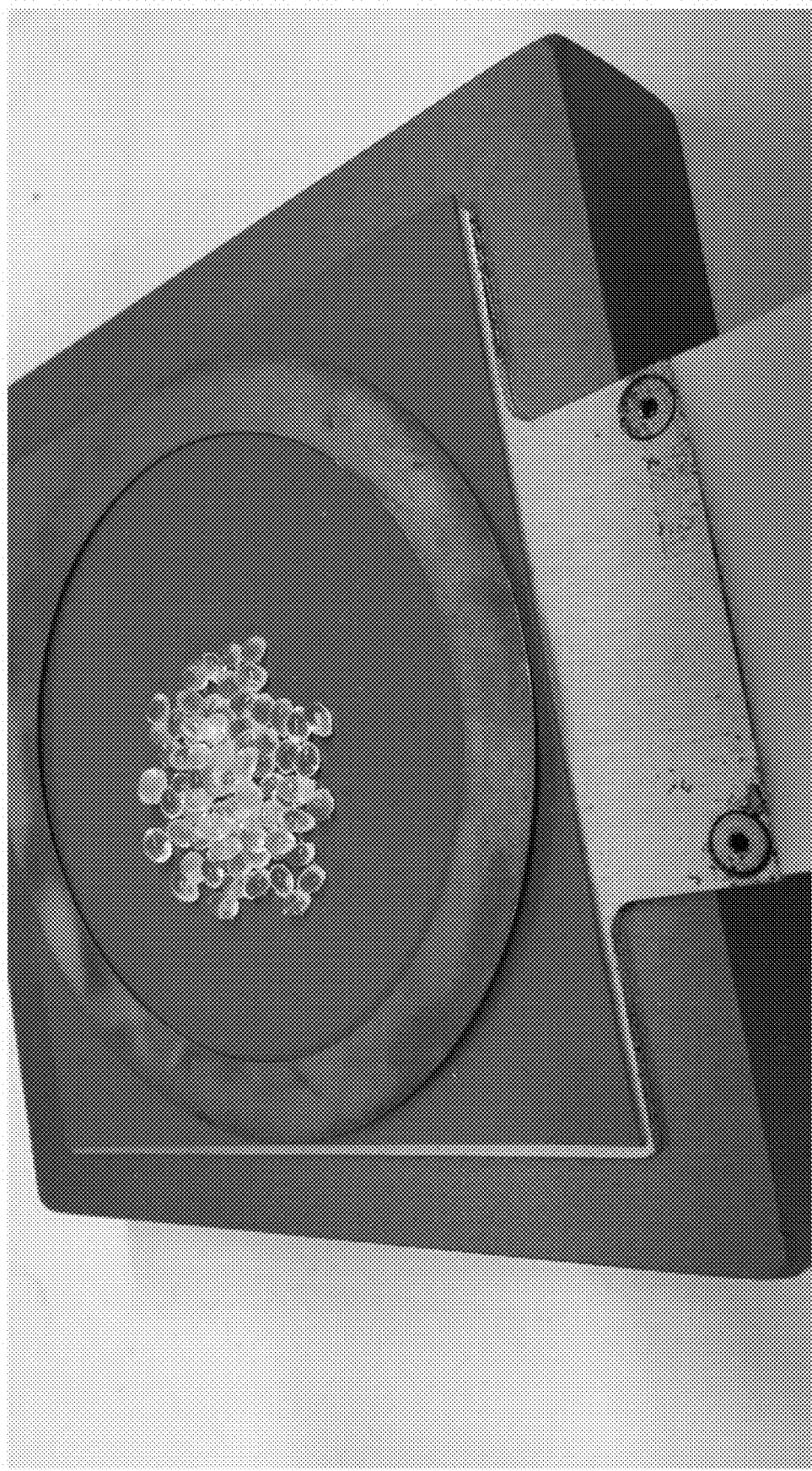
Figure 6:
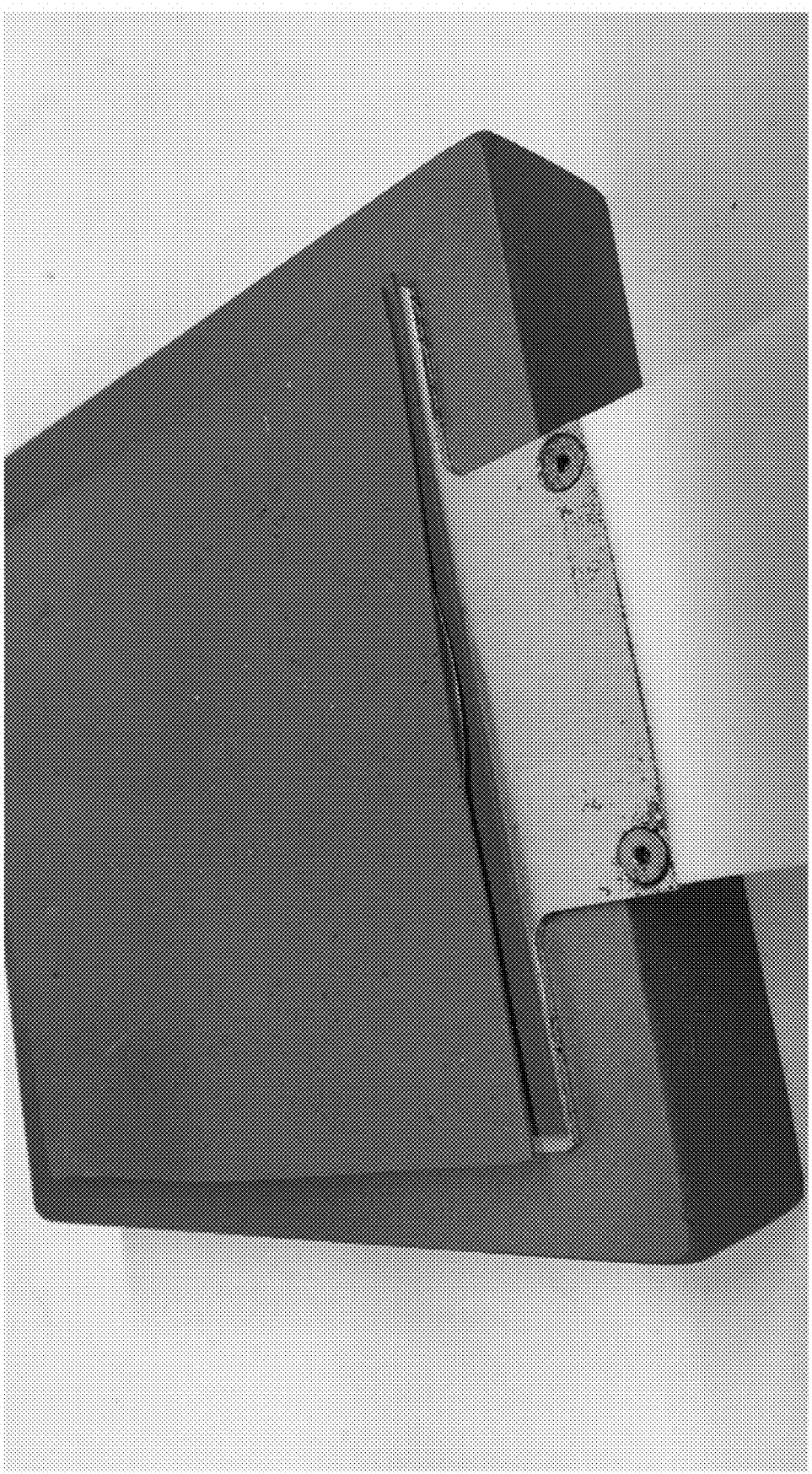
Figure 7:
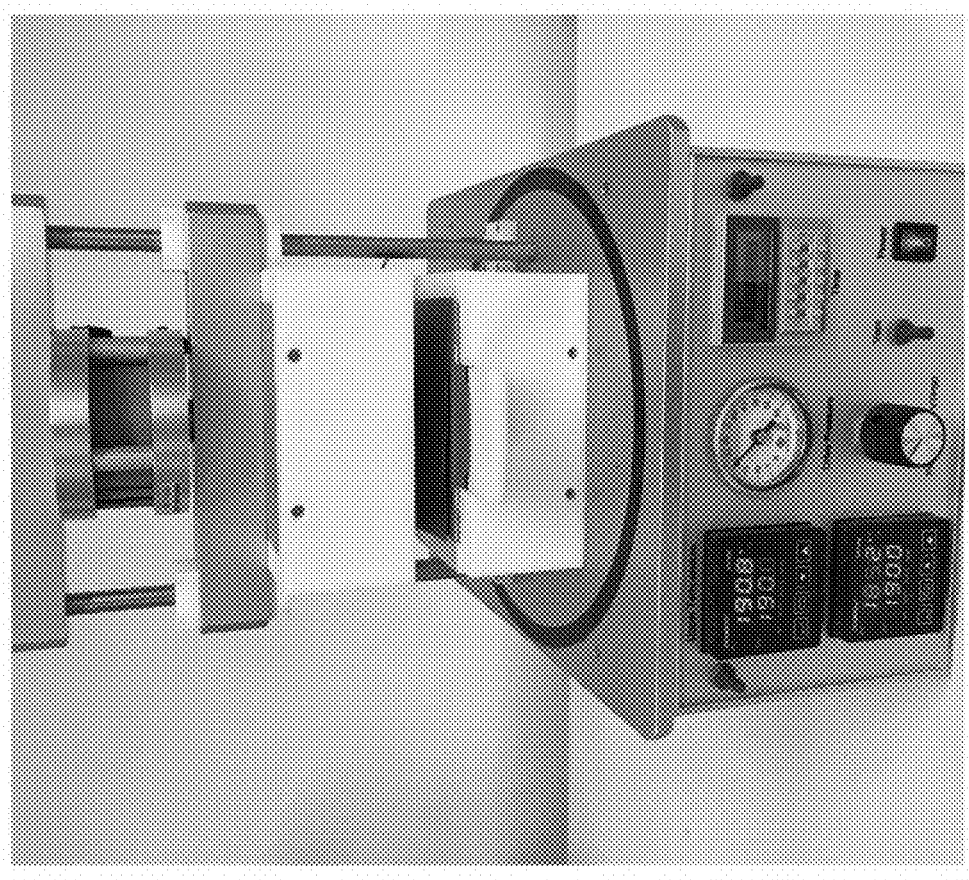
Figure 7:
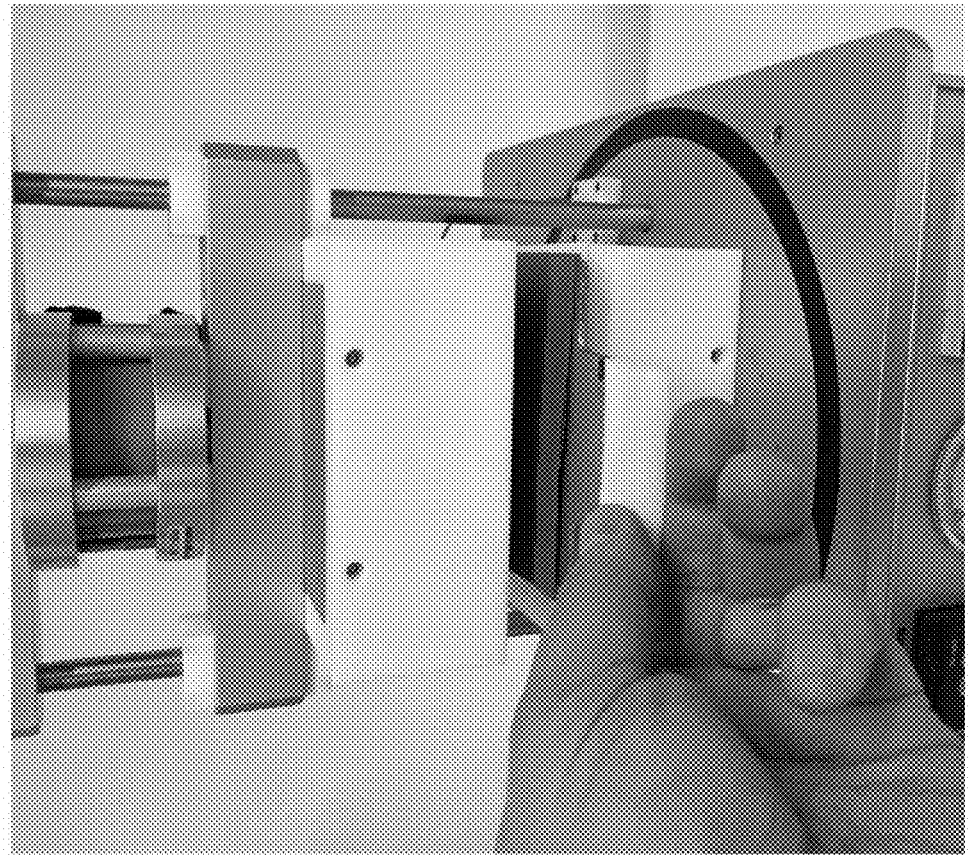
Figure 8:
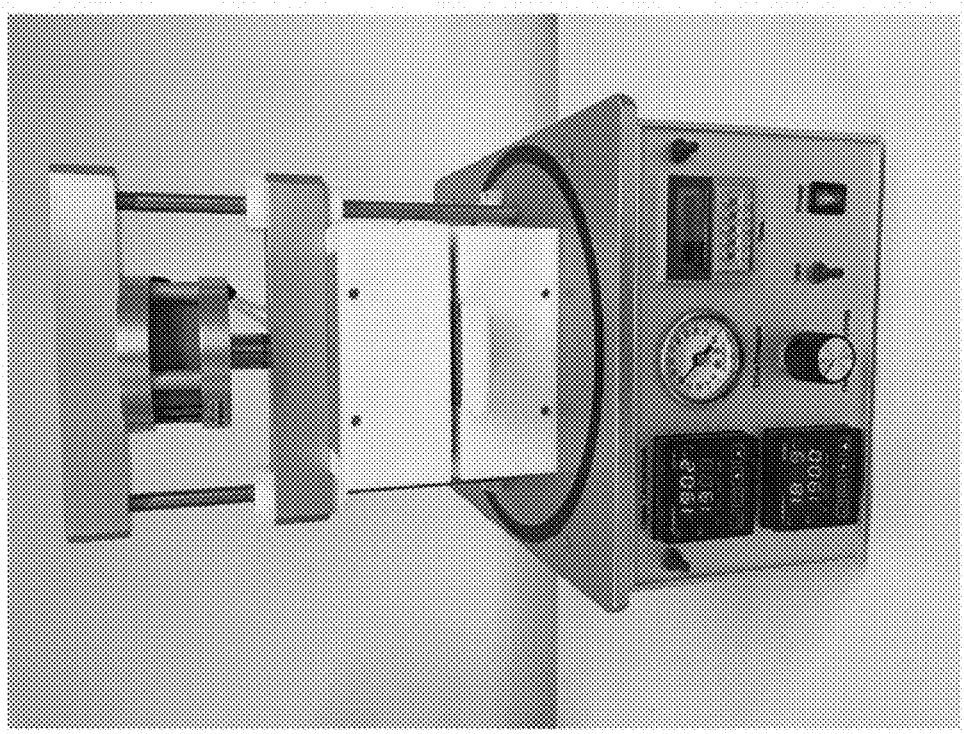
Figure 9:
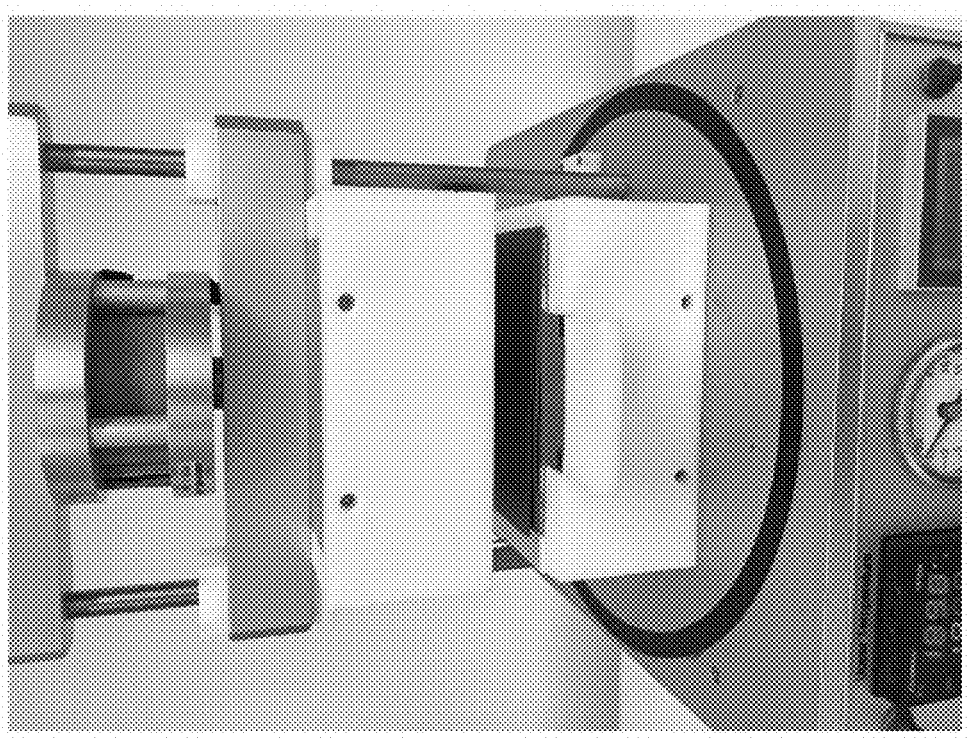
Figure 10:
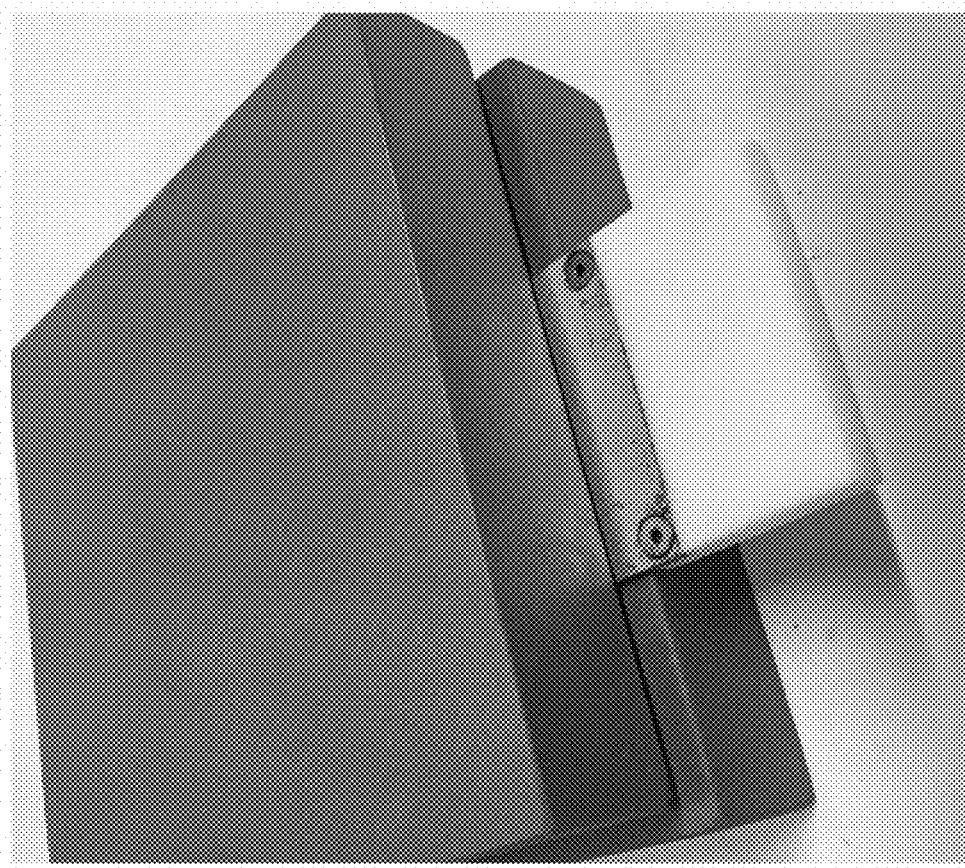
Figure 10:
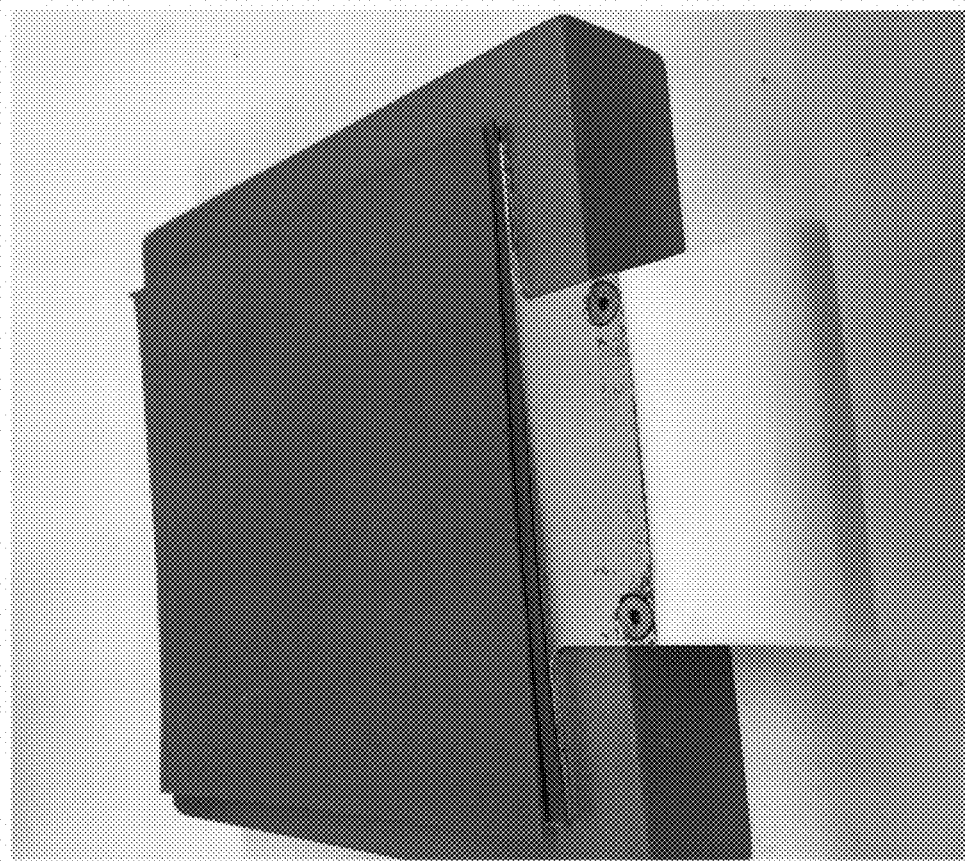
Figure 11:
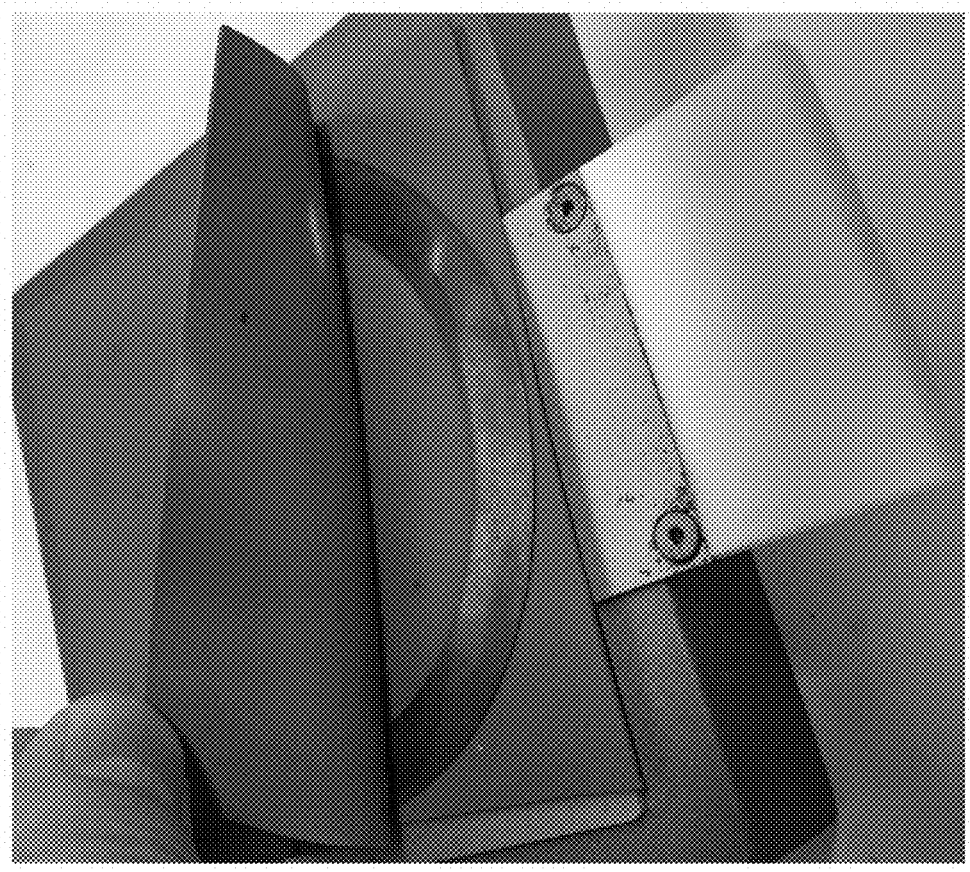
Figure 11:
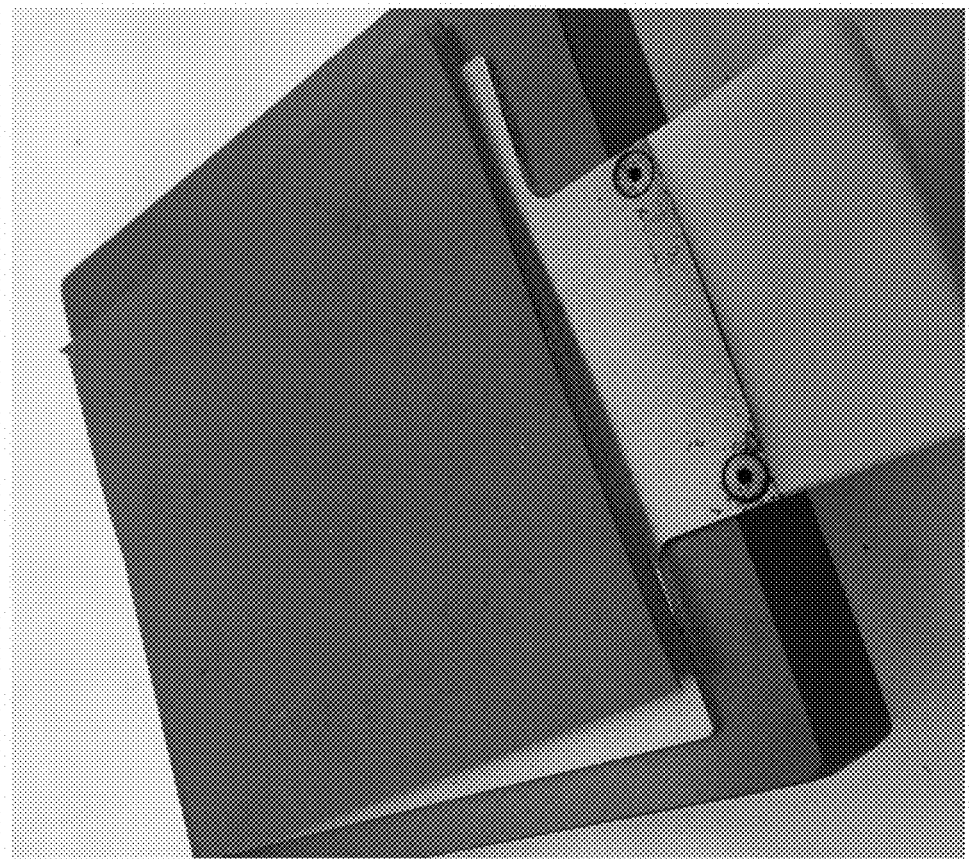
Figure 12:
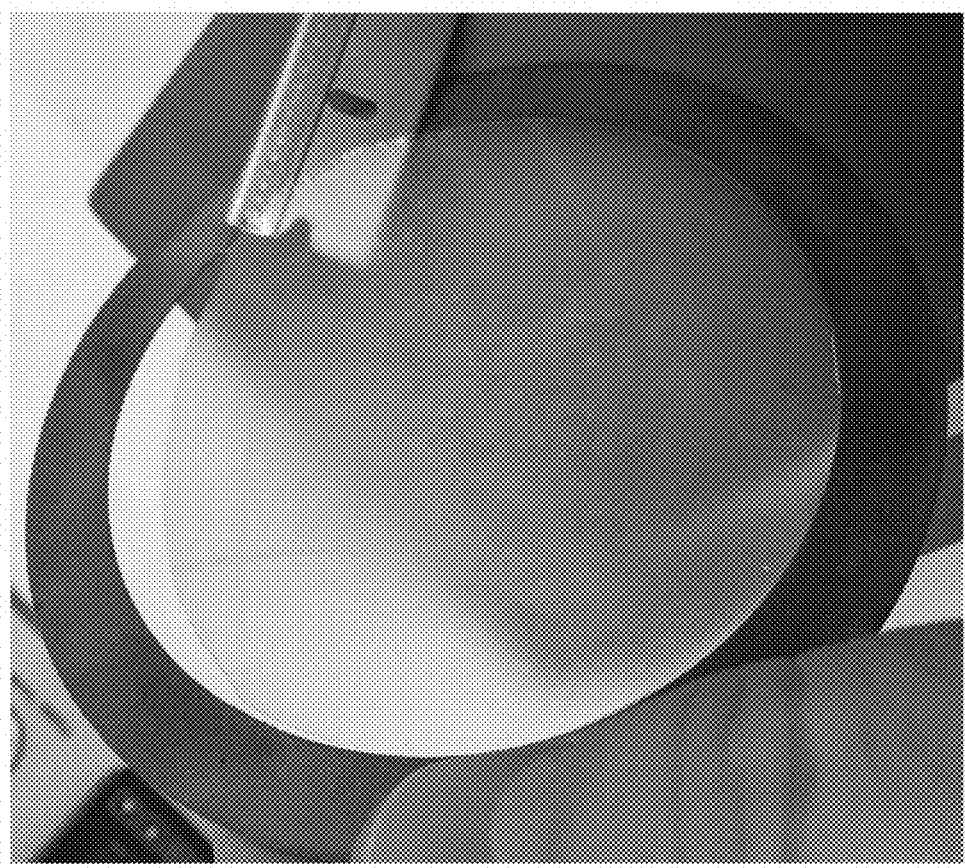
Figure 12:
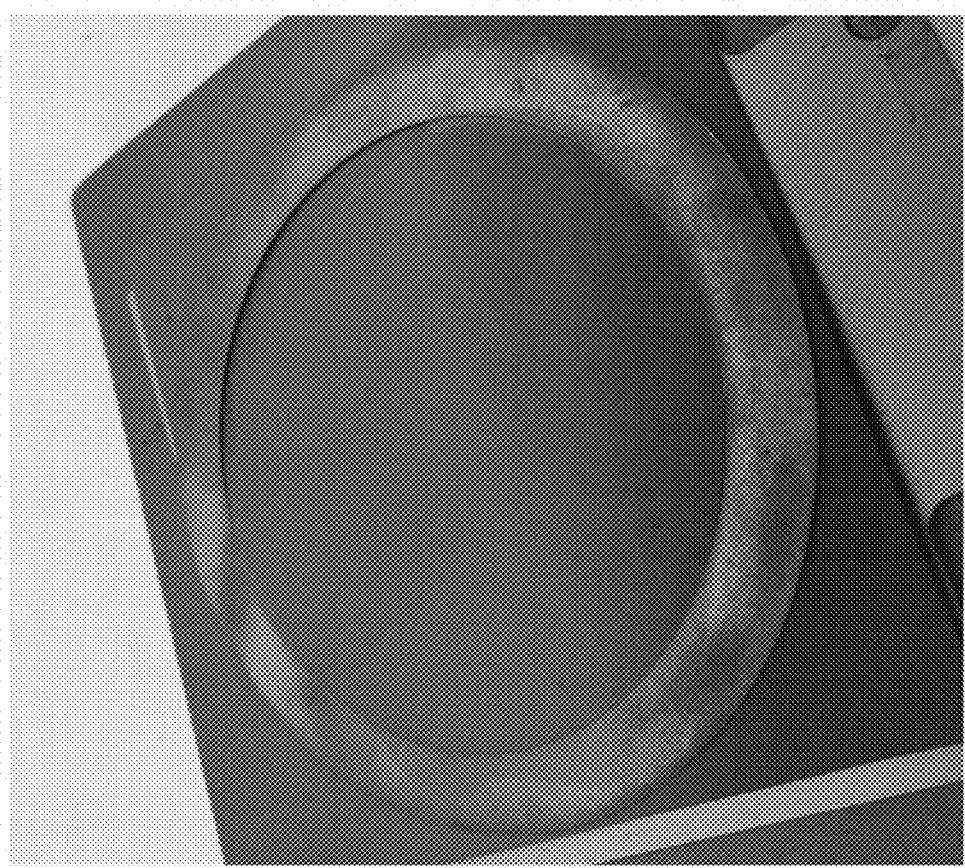
Figure 13:
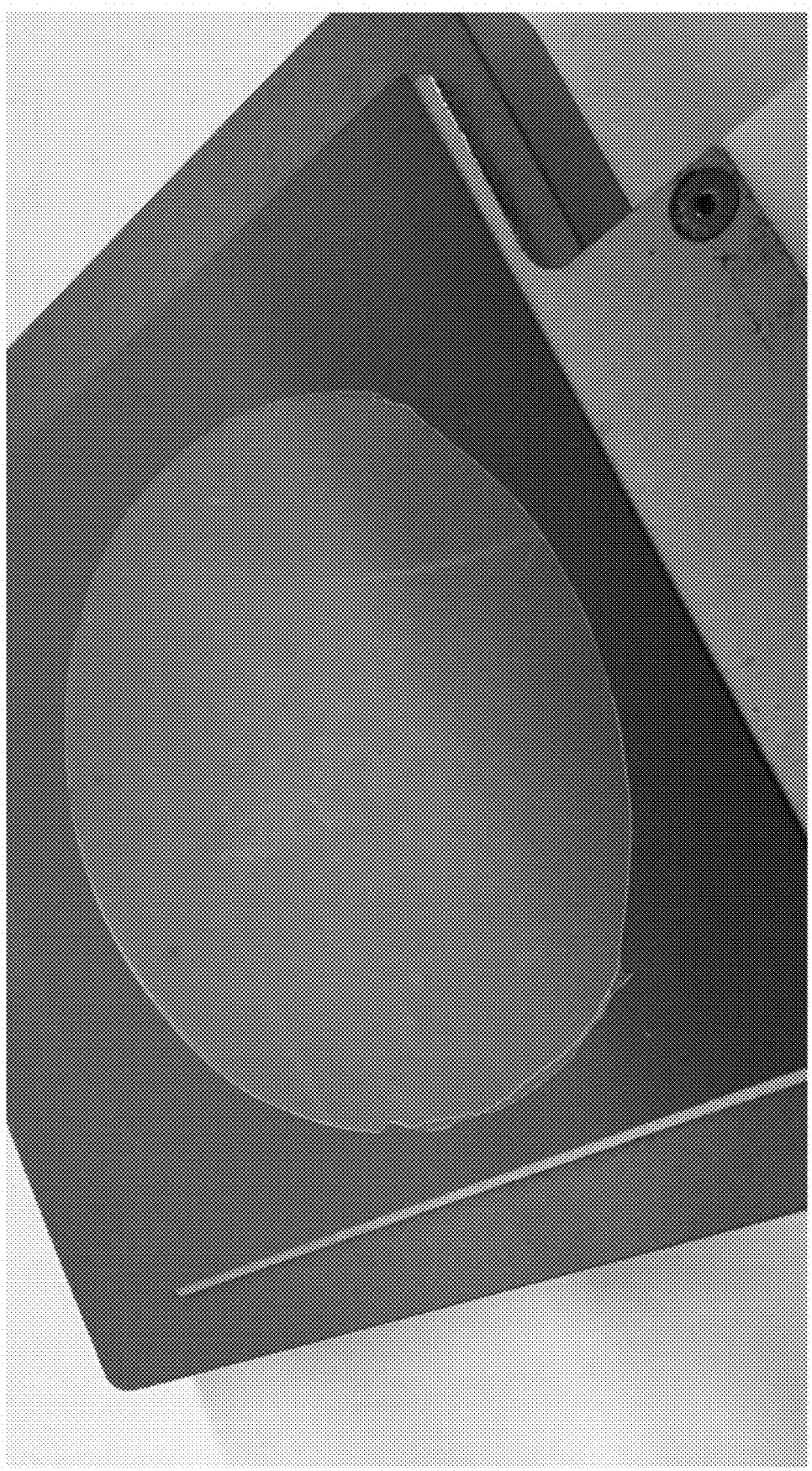

ChronoFlex AL 75A thermoplastic polyurethane pellets were obtained (AdvanSource Biomaterials, Wilmington, Mass.) and approximately 2 grams of these pellets were placed onto a 0.8 mm thick silicone film pre-cut to a 100 mm by 100 mm square. A 0.3 mm thick steel ring was then placed onto the silicone film (FIG. 5) and then a second 0.8 mm thick silicone square was placed on top of the pellets (FIG. 6). This assembly was then placed between two platens (FIG. 7) pre-heated to 190° C. on a Fluidic Tools VTP-50 thermal press (Aixtek, Allston, Mass.). After 5 minutes incubation the platens were closed and approximately 0.3 MPa was applied to the assembly. This pressure was maintained for 5 additional minutes (FIG. 8) and released (FIG. 9). The assembly was then placed between two metallic platens and allowed to cool to room temperature over several minutes. After cooling, the film was separated from the assembly and steel spacer (FIGS. 11-13).

Example 2

Cutting the Elastomeric Film

Figure 14:
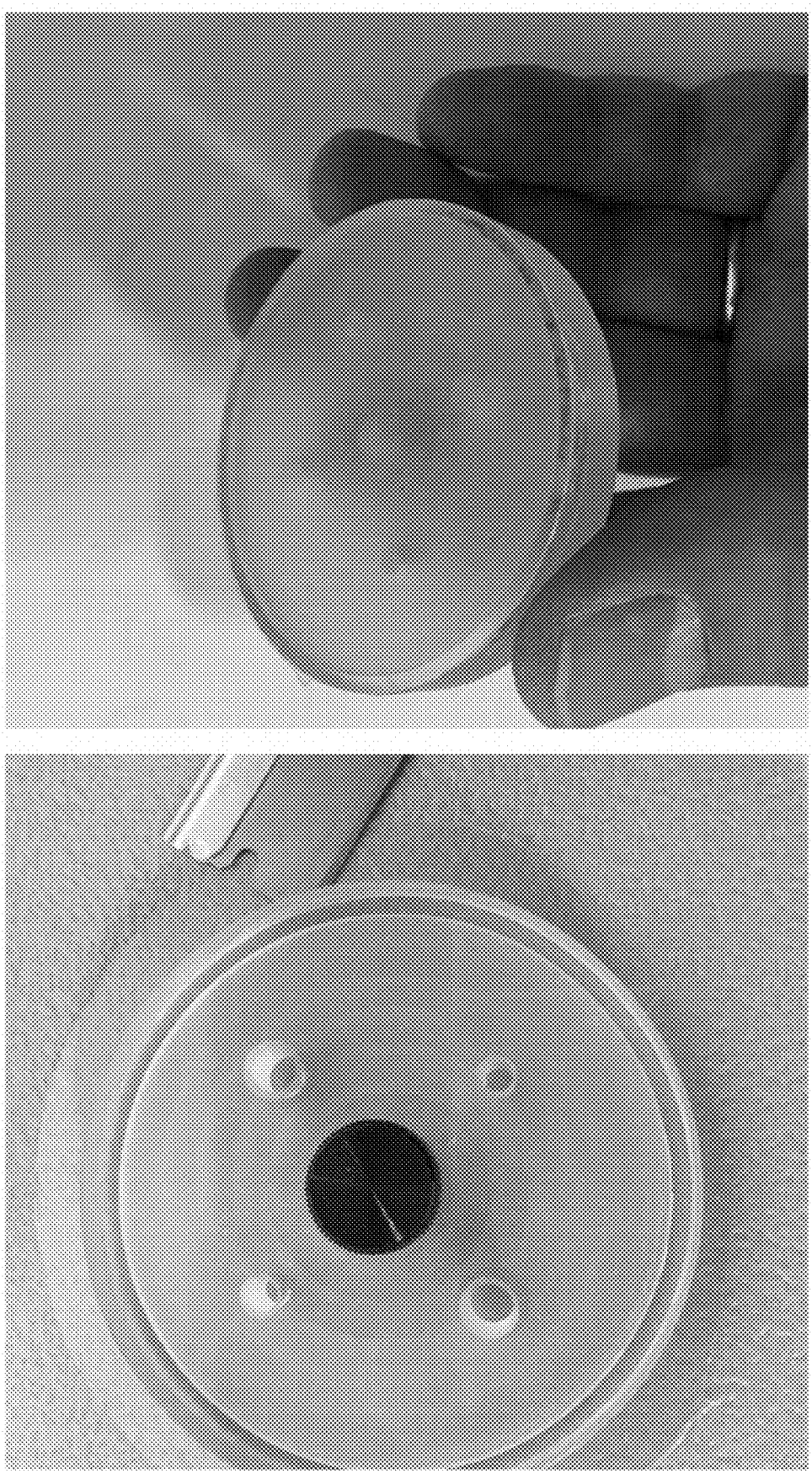
Figure 15:
Figure 16:
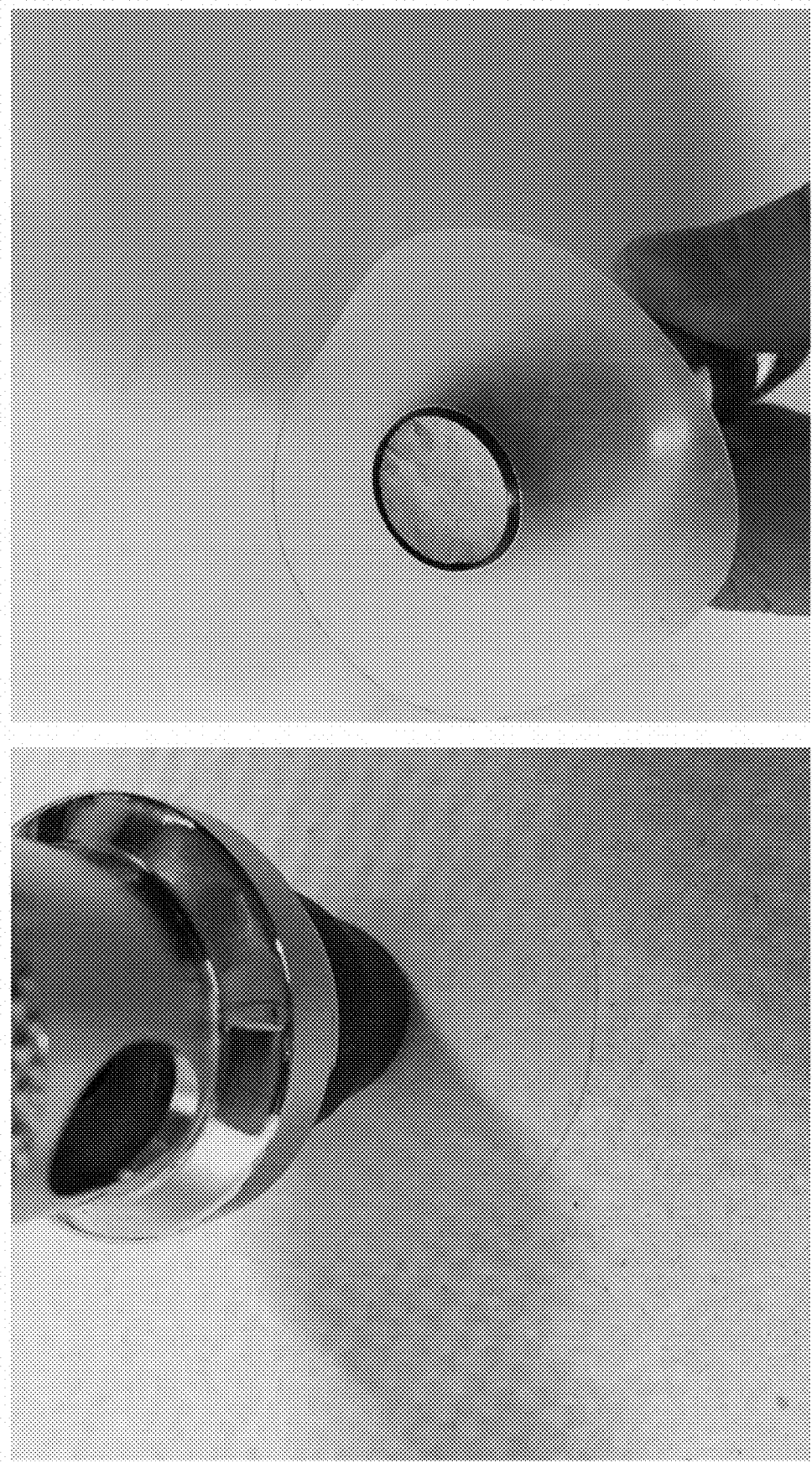

A template (61 mm diameter) was placed onto the elastomeric film (FIG. 14) and used to cut a circular shape (FIG. 15). A steel die (18 mm diameter) was used to punch a hole into the circular shape (FIG. 16).

Example 3

Forming an Elastomeric Shape

Figure 17:
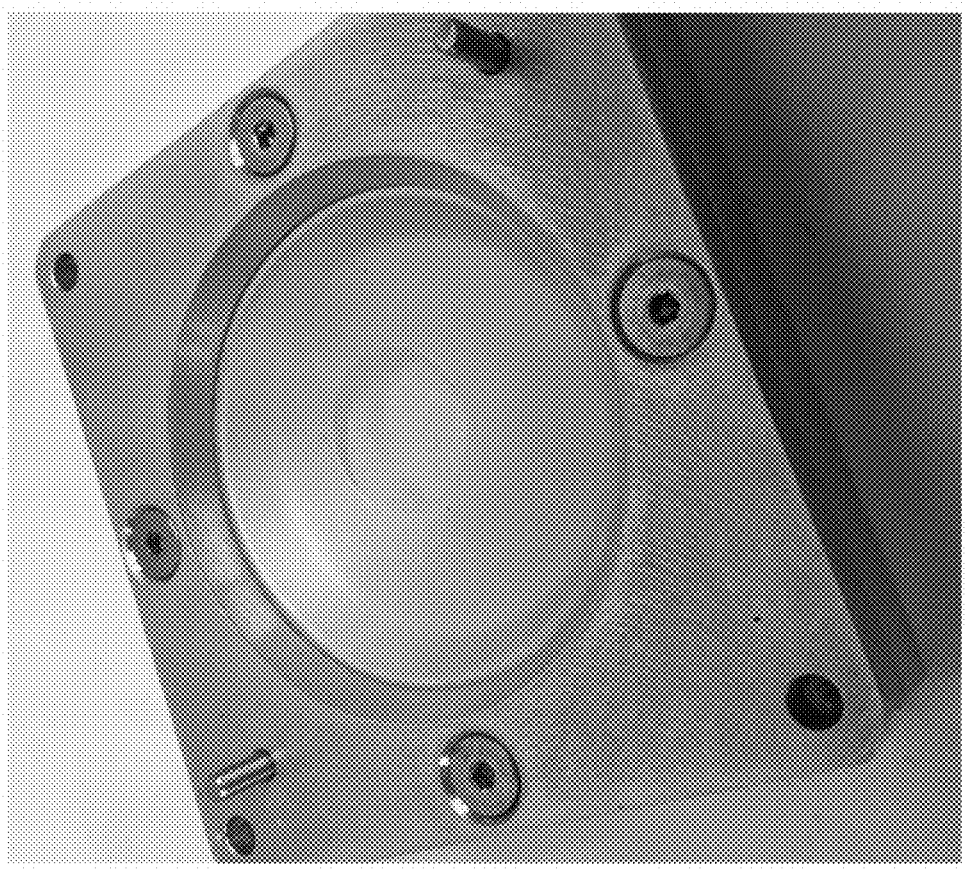
Figure 17:
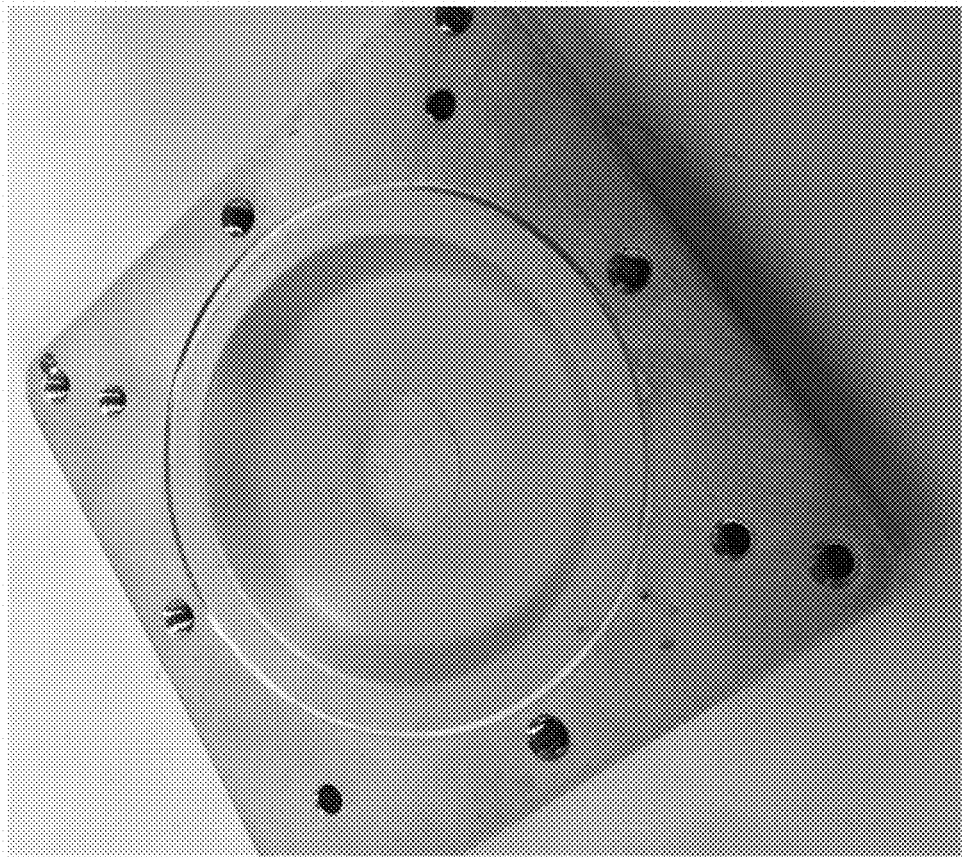
Figure 18:
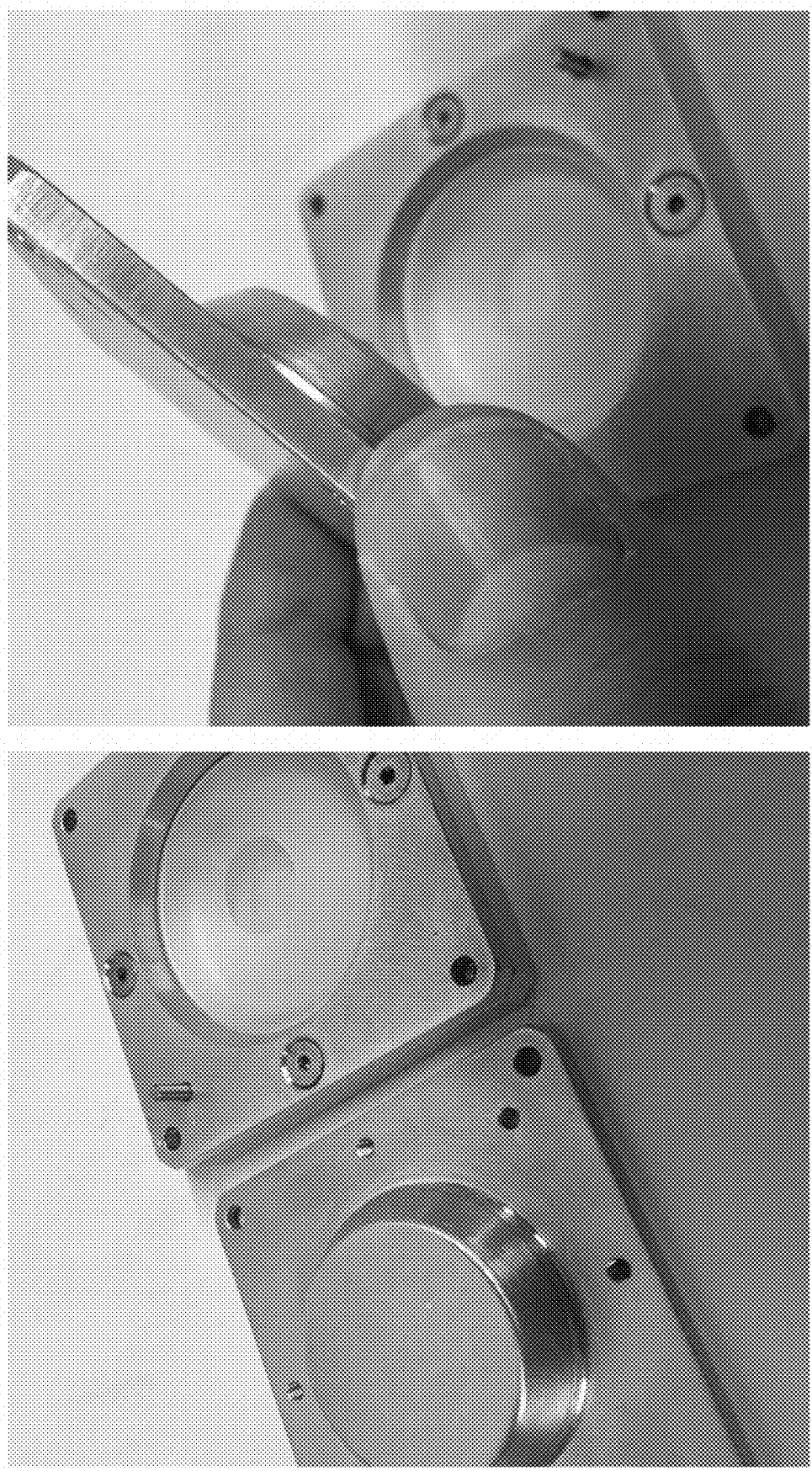
Figure 19:
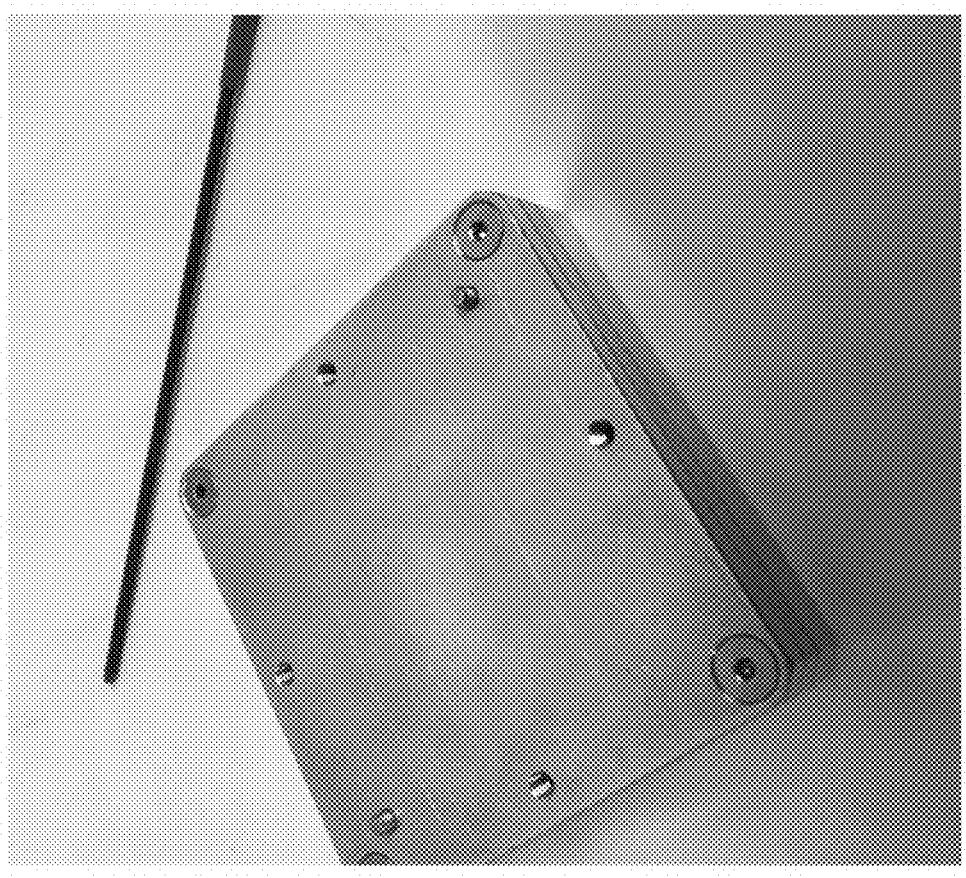
Figure 19:
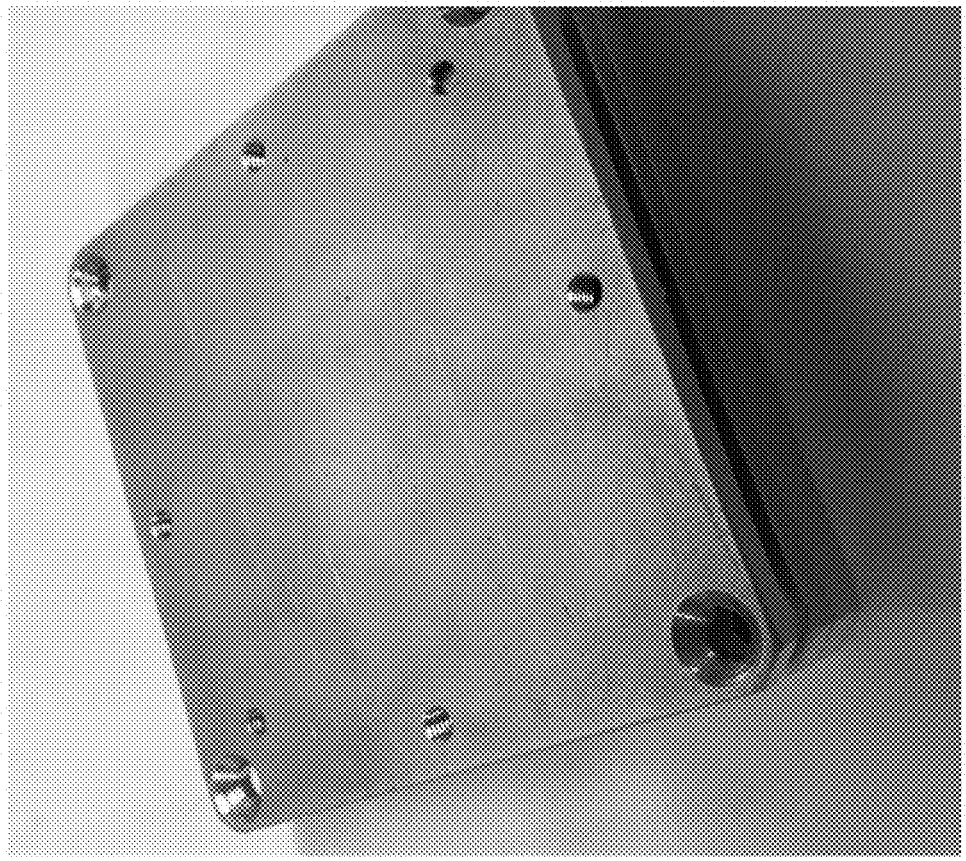
Figure 20:
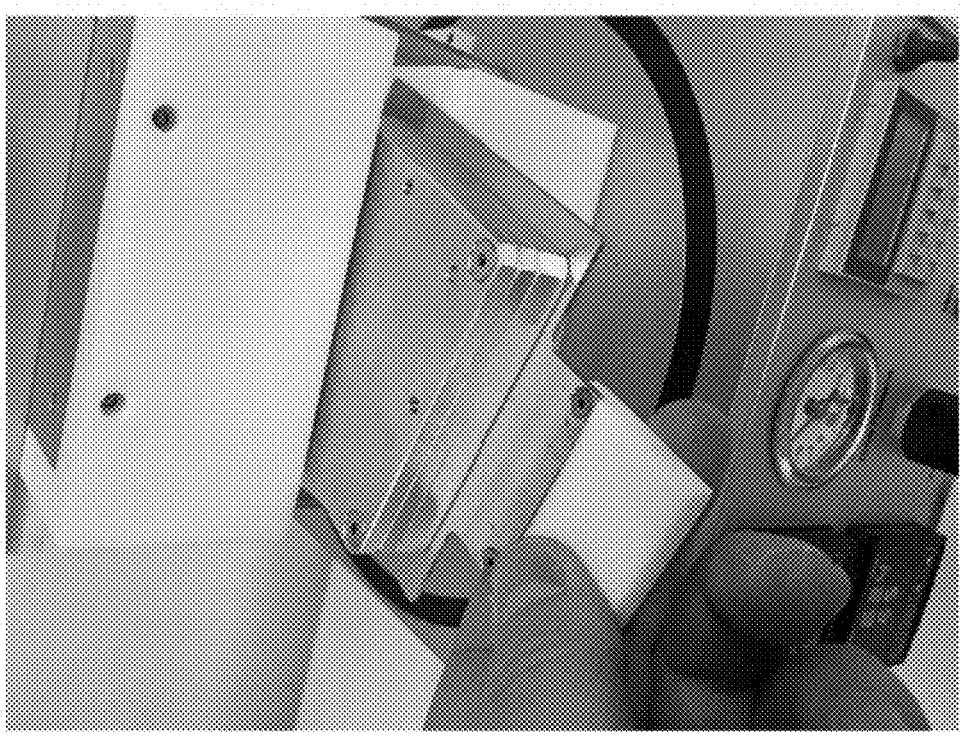
Figure 21:
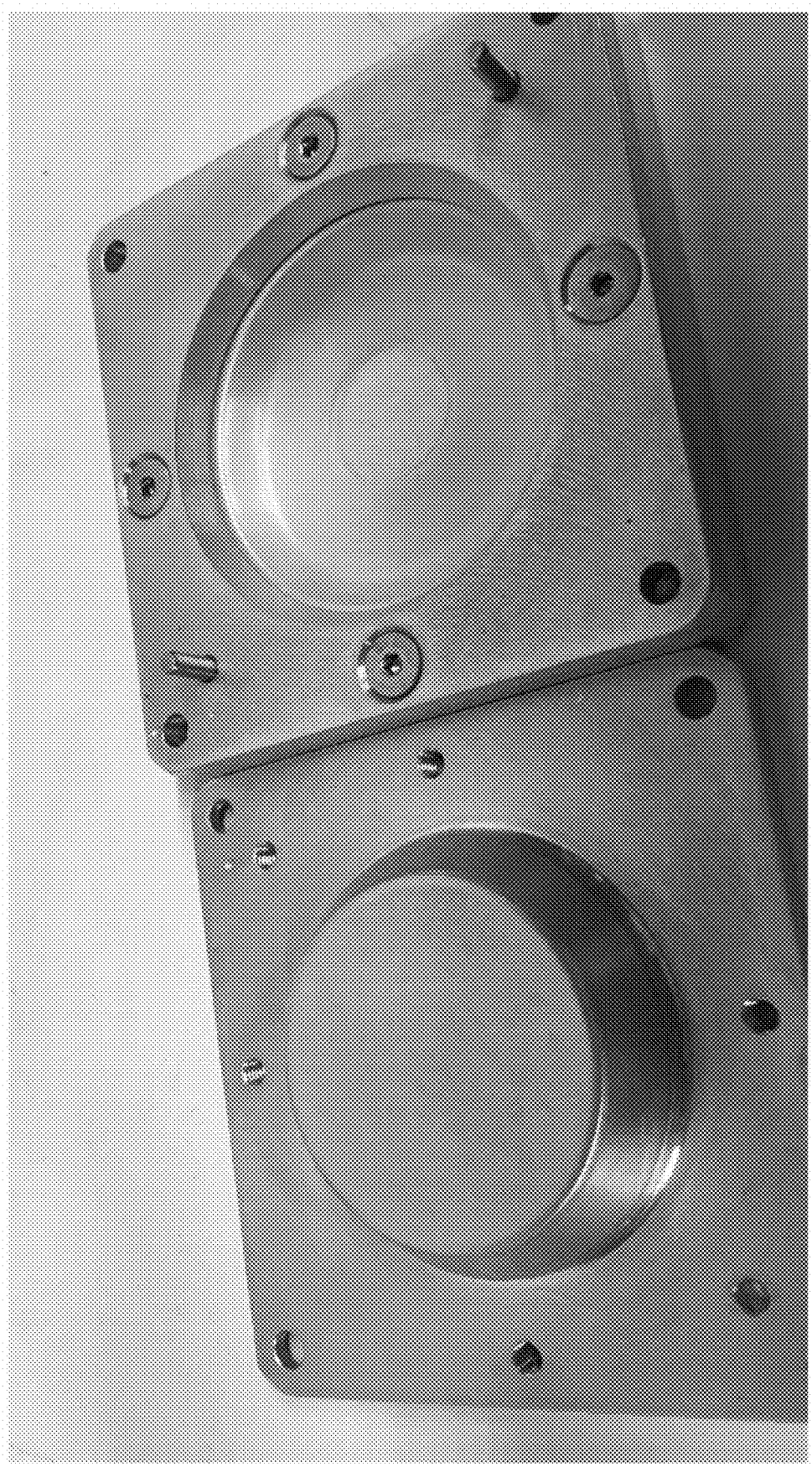
Figure 22:
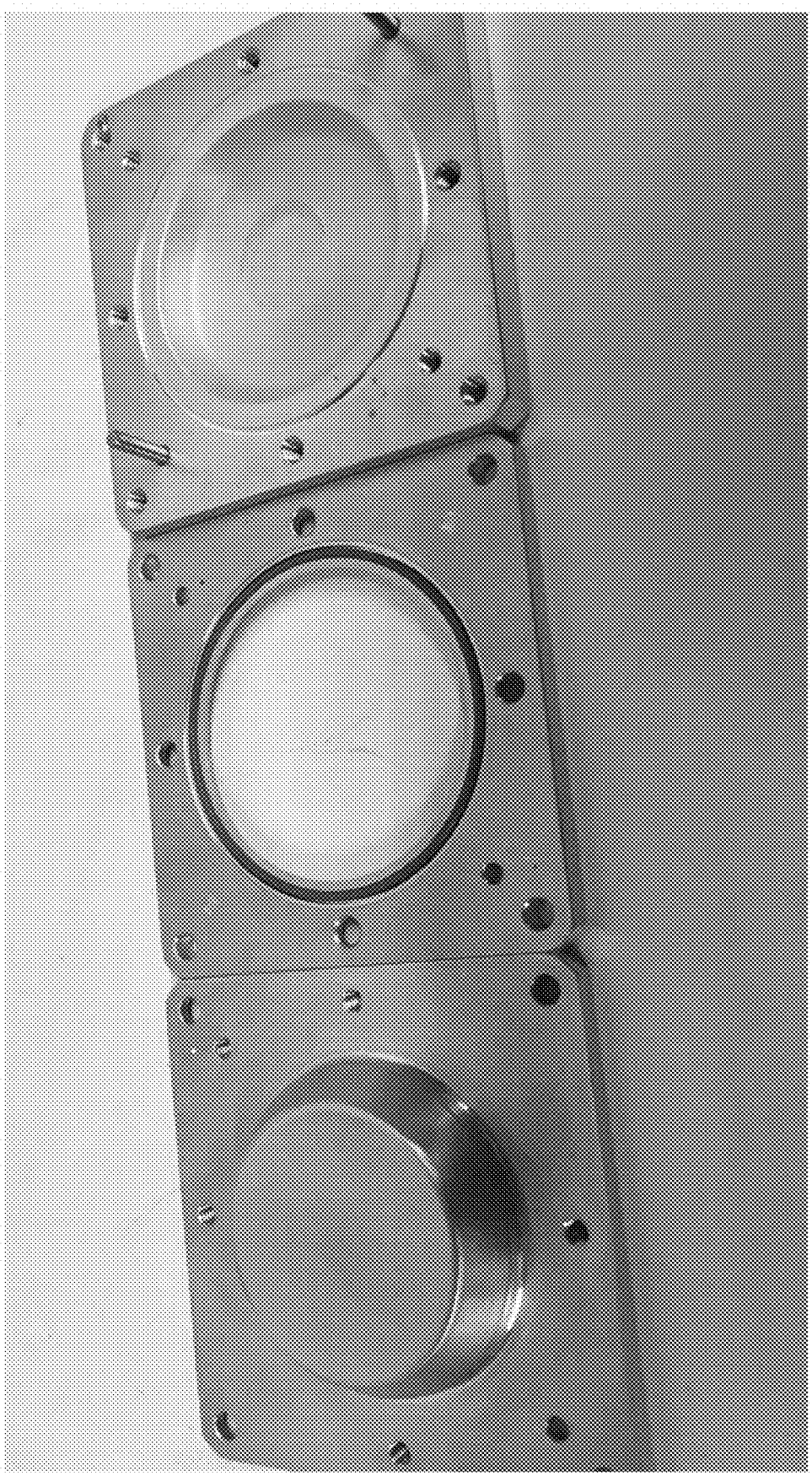
Figure 23:
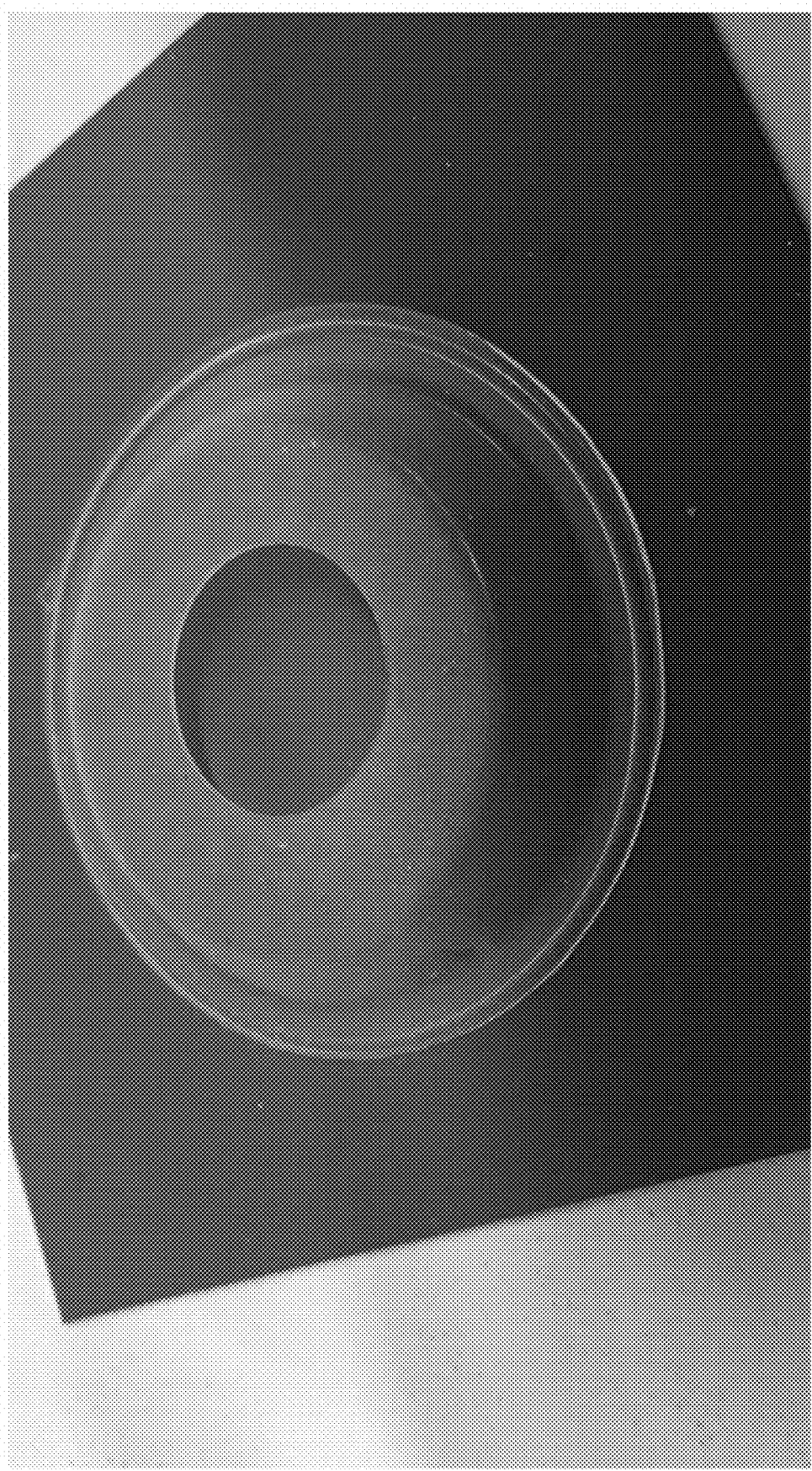

The cut elastomeric film was placed onto the rim of an aluminum support with a 6.8 mm deep cavity. The sidewalls that join the cavity to the rim were designed with a 20 degree draft angle. A clamping frame was placed onto the supported film and bolted to the aluminum support (FIG. 17). The clamping frame was designed with a silicone o-ring that, under pressure, gripped the elastomeric film and allowed it to be shaped by an aluminum boss (FIG. 18) driven against the held film (FIG. 19). The clamped aluminum assembly was placed between the heated platens (65° C.) of a Fluidic Tools thermal press (Aixtek, Allston, Mass.) and maintained at this temperature for 10 minutes (FIG. 22). The aluminum forming assembly was then taken apart (FIGS. 21 and 122) and the shaped elastomer was removed from the assembly (FIG. 23).

Example 4

Joining a Dialysis Membrane onto a Shaped Elastomer

Figure 24:
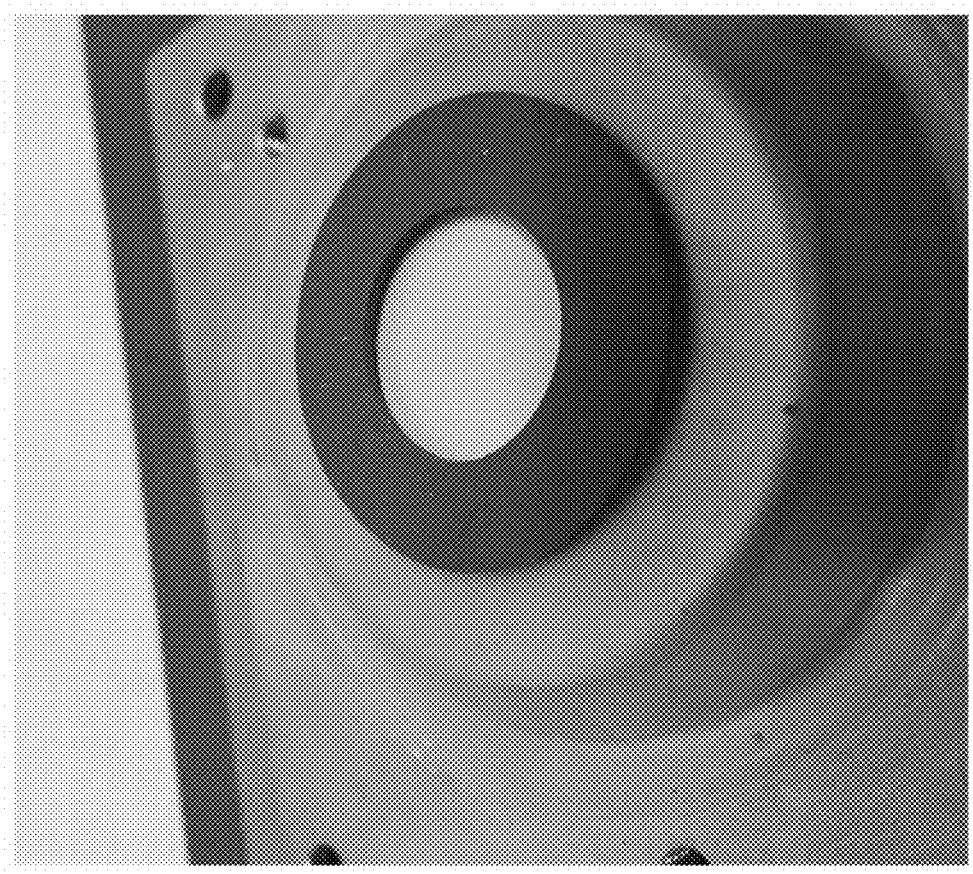
Figure 24:
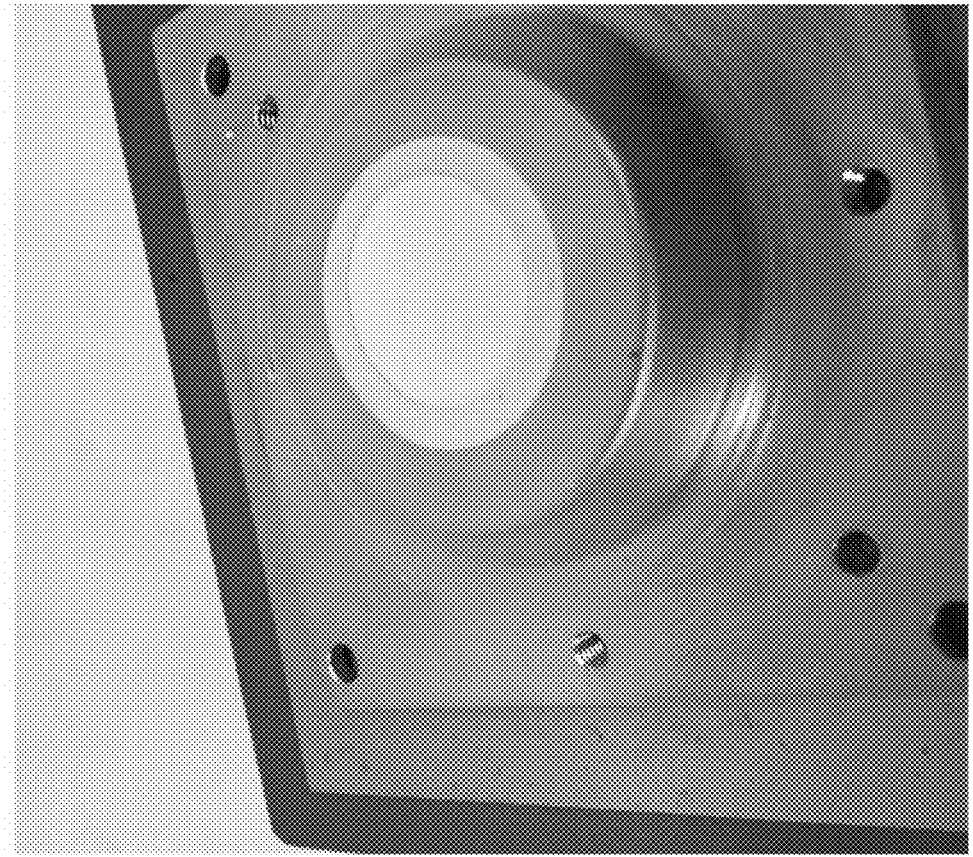
Figure 25:
Figure 26:
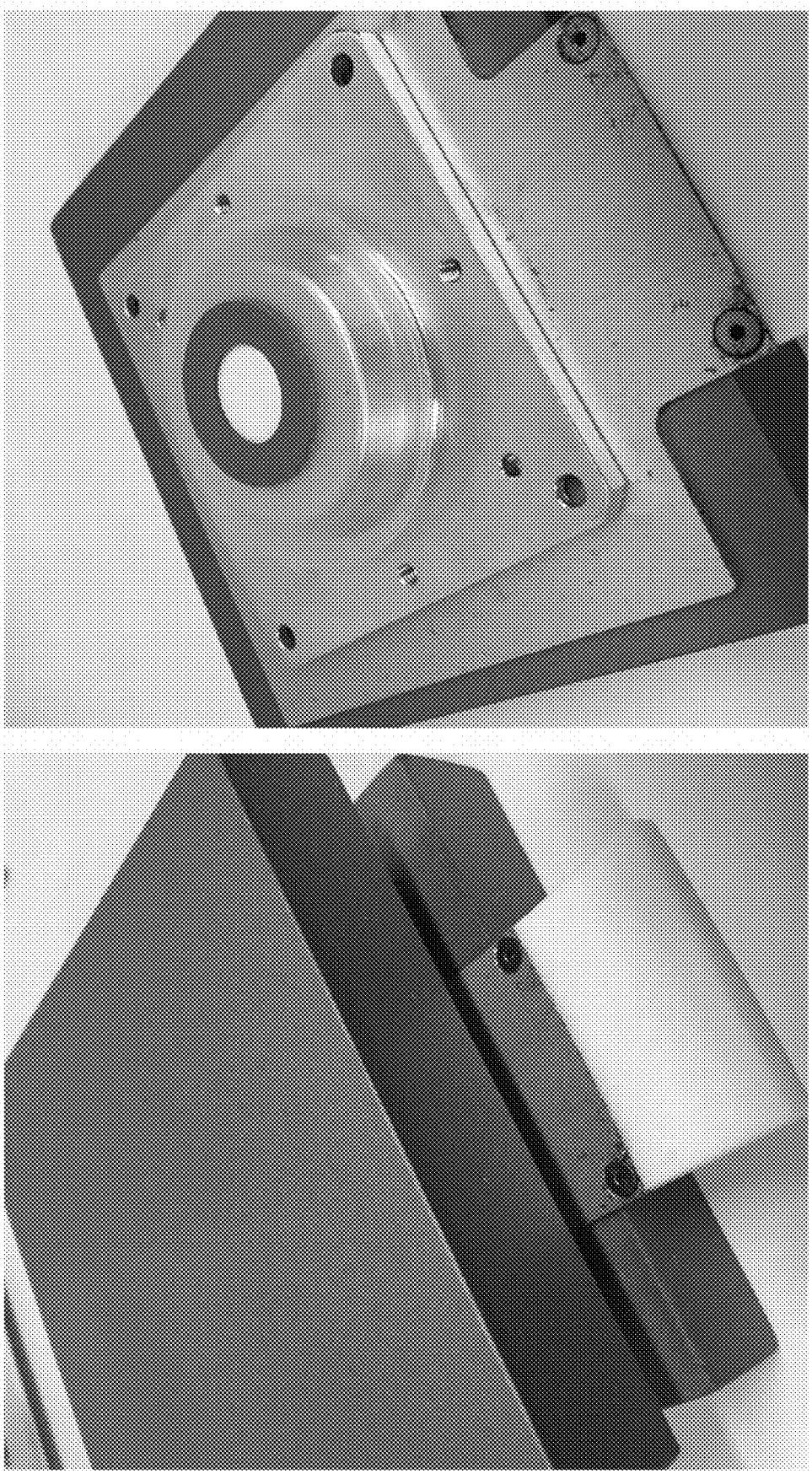
Figure 27:
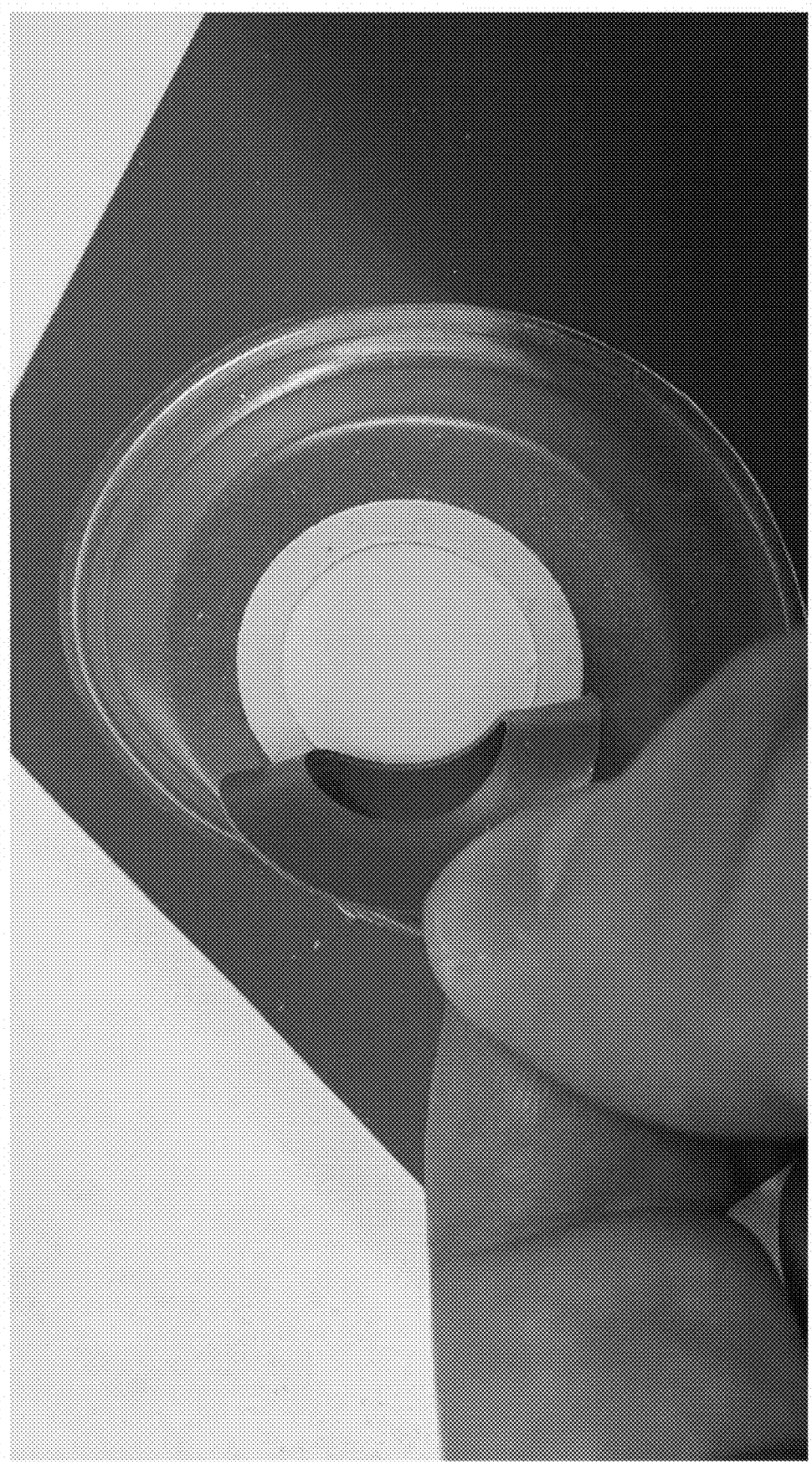
Figure 28:
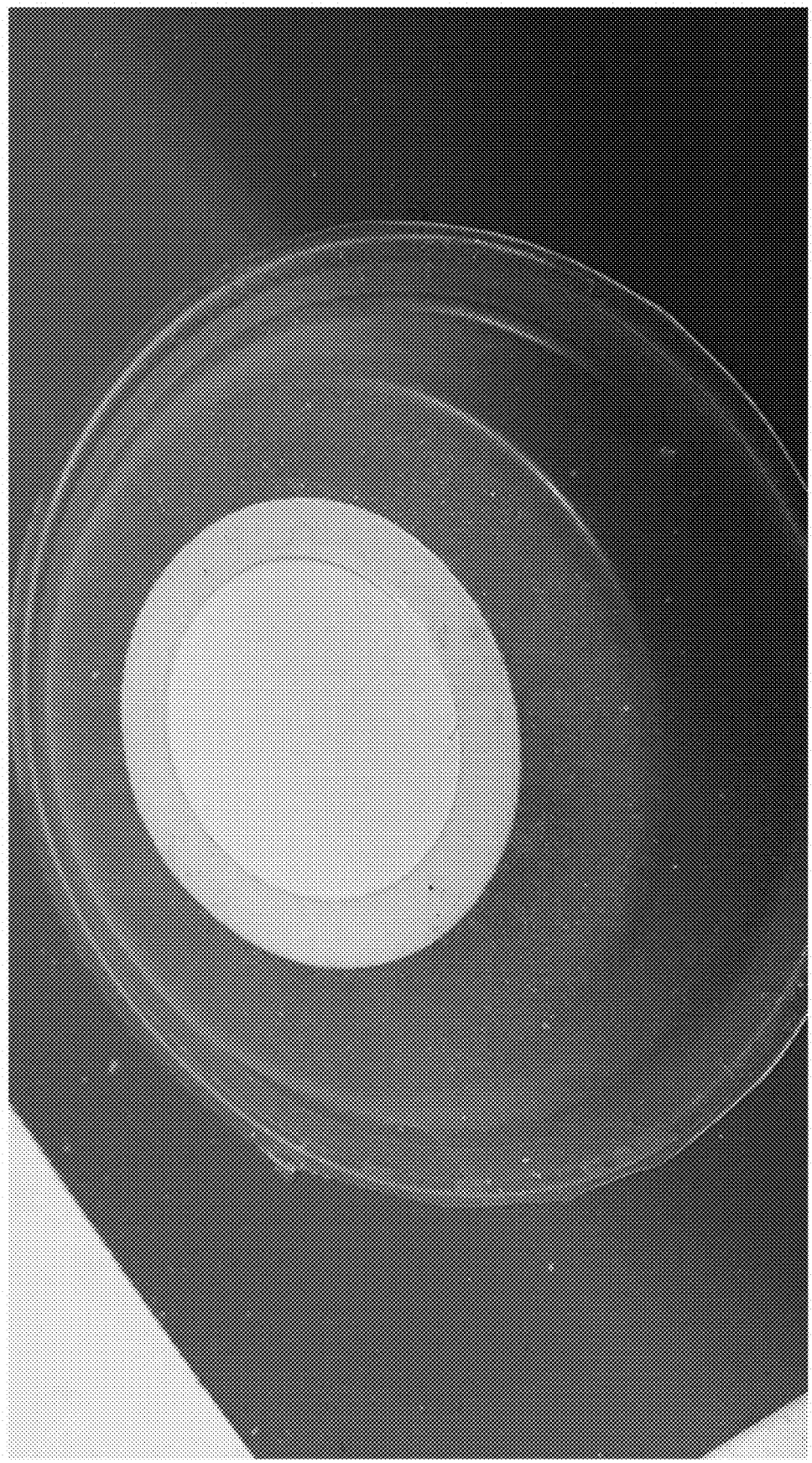
Figure 29:

A 28 mm diameter polyethersulfone dialysis membrane with a 30,000 molecular weight cut-off (Sartorius, Goettingen, Germany) was placed onto the aluminum boss of the prior examples. The shaped elastomer was placed onto the dialysis membrane resting on the aluminum boss and a 0.8 mm thick silicone ring was placed onto the shaped elastomer (FIG. 24). This assembly was placed between the heated platens (205° C.) and pressure was applied for 10 seconds (FIG. 25). The assembly was then cooled between thermally conductive platens, initially maintained at room temperature (FIG. 26), and the silicone ring was removed from the joined dialysis membrane (FIGS. 27-29).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A dialysis device implantable in a patient for dialysis, comprising a filtration unit, the filtration unit comprising:
    a top dialysis chamber and a bottom dialysis chamber for containing and/or circulating dialysate; and
    a blood chamber for containing and/or circulating blood of the patient, disposed between the top dialysis chamber and the bottom dialysis chamber and being in communication with the top dialysis chamber and the bottom dialysis chamber, respectively,
    wherein each of the top dialysis chamber, the bottom dialysis chamber and the blood chamber comprises at least one inlet for circulating fluid into and/or out of each of the top dialysis chamber, the bottom dialysis chamber and the blood chamber; and
    wherein the top dialysis chamber, the bottom dialysis chamber and the blood chamber are configured such that the blood in the blood chamber and the dialysate in the top dialysis chamber and the bottom dialysis chamber operably interact with each other for dialysis.

2. The dialysis device of claim 1, wherein the filtration unit further comprises first and second ultrafiltration membranes, wherein the first ultrafiltration membrane is disposed between the top dialysis chamber and the blood chamber and the second ultrafiltration membrane is disposed between the blood chamber and the bottom dialysis chamber such that the blood contained in the blood chamber is in contact with surfaces of the first and second ultrafiltration membranes that face the blood chamber, the dialysate fluid contained in the top dialysis chamber is in contact with a surface of the first ultrafiltration membrane that face the top dialysis chamber, and the dialysate fluid contained in the bottom dialysis chamber is in contact with a surface of the second ultrafiltration membrane that face the bottom dialysis chamber.

3. The dialysis device of claim 2, wherein the filtration unit further comprises first and second diaphragms adapted to support the first and second ultrafiltration membranes, respectively, and formed of a flexible inert material that allows the blood chamber to fill during expansion or to expel during contraction, while having opposite expansion or contraction effect on the top and bottom dialysis chambers.

4. The dialysis device of claim 2, wherein each ultrafiltration membrane is a porous membrane having pores that permit molecules to travel between the blood chamber and the top dialysis chamber, and between the blood chamber and the bottom dialysis chamber, whereby substances in the blood to be removed from the blood are passable from the blood in the blood chamber to the dialysate in the top dialysis chamber and the bottom dialysis chamber, or substances in the dialysate to be added into the blood are passable from the dialysate in the top dialysis chamber and the bottom dialysis chamber into the blood chamber.

5. The dialysis device of claim 4, wherein each ultrafiltration membrane is formed of electrospun fleece, or nanofibers of a polymer or a polymer composite material.

6. The dialysis device of claim 4, wherein each ultrafiltration membrane is formed of polyurethane.

7. The dialysis device of claim 4, wherein the pores of each ultrafiltration membrane are less than about 30 kDa in diameter.

8. The dialysis device of claim 4, wherein each ultrafiltration membrane is further adapted as a pressure barrier separating fluid volumes contained in the top dialysis chamber and/or the bottom dialysis chamber from that of the blood chamber.

9. The dialysis device of claim 1, wherein the at least inlet of the blood chamber is operably connected to a vascular system of the patient, the at least one inlet of the top dialysis chamber and/or the bottom dialysis chamber are operably connected to a dialysate reservoir, so that blood of the patient is flowable into and/or out of the blood chamber, the dialysate in the dialysate reservoir is flowable into and/or out of the top dialysis chamber and/or the bottom dialysis chamber, whereby unwanted substances of the blood in the blood chamber are exchangeable with the dialysate in the top dialysis chamber and/or the bottom dialysis chamber as the blood flows into and/or out of the blood chamber.

10. The dialysis device of claim 1, wherein the at least inlet of the blood chamber comprises an inlet and an outlet each having a valve configured such that when the blood chamber fills with fresh or uncleansed blood, the valve of the inlet is opened, while the valve of the outlet is closed, and when the blood chamber expels the purified blood, the valve of the outlet is opened, while the valve of the inlet is closed.

11. The dialysis device of claim 1, wherein the filtration unit further comprises a top housing, a bottom housing and a middle housing sealingly connected between the top housing and the bottom housing, wherein the top housing, the bottom housing and the middle housing house the top dialysis chamber, the bottom dialysis chamber and the blood chamber, respectively.

12. The dialysis device of claim 11, wherein each of the top housing and the bottom housing have an opening that provides a means to sealingly affix an outer membrane to each of the top housing and the bottom housing.

13. The dialysis device of claim 11, wherein the middle housing has at least an incompressible portion at the at least one inlet of the blood chamber for enhancing flow of the blood into and/or out of the blood chamber.

14. The dialysis device of claim 1, further comprising at least one pump coupled to at least one of the top dialysis chamber and the bottom dialysis chamber for conveying the dialysate to and/or from the top dialysis chamber and the bottom dialysis chamber.

15. The dialysis device of claim 14, wherein the at least one pump is further coupled to an internal dialysate reservoir and/or an external dialysate reservoir.

16. The dialysis device of claim 15, wherein the at least one pump is positioned between the top and/or bottom dialysis chambers and the internal or external dialysate reservoir.

17. The dialysis device of claim 14, wherein the at least one pump is attachable either fixedly within the body of the patient or removably outside the patient.

18. The dialysis device of claim 14, wherein the at least one pump is fixedly attachable to at least one of the top dialysis chamber and the bottom dialysis chamber.

19. The dialysis device of claim 14, wherein the at least one pump is programmed to alternatively cause the top dialysis chamber and the bottom dialysis chamber to pump and expel the dialysate in a cycle of pre-determined periodicity, thereby causing the blood chamber to alternately fill with and expel the blood for the dialysis.

20. The dialysis device of claim 19, wherein the at least one pump is further programmed to periodically pump a larger dialysate volume into the top dialysis chamber and the bottom dialysis chamber, thereby resulting in a higher pressure in the top dialysis chamber and the bottom dialysis chamber than in the blood chamber.

21. The dialysis device of claim 19, wherein the at least one pump is further programmed to periodically pump a larger dialysate volume into the at least one dialysis chamber, thereby resulting in a higher pressure in the at least one dialysis chamber than in the at least one blood chamber.

22. A dialysis device implantable in a patient for dialysis, comprising a filtration unit, the filtration unit comprising:
    at least one dialysis chamber for containing and/or circulating dialysate; and
    at least one blood chamber for containing and/or circulating blood of the patient, disposed on at least one dialysis chamber and being in communication with the at least one dialysis chamber,
    wherein each of the at least one dialysis chamber and the at least one blood chamber comprise at least one inlet for circulating fluid into and/or out of the at least one dialysis chamber and the at least one blood chamber; and
    wherein the at least one dialysis chamber and the at least one blood chamber are configured such that the blood in the at least one blood chamber and the dialysate in the at least one dialysis; wherein at least one dialysis chamber comprises two or more dialysis chambers, and the at least one blood chamber comprises two or more blood chambers, and wherein the two or more dialysis chambers and the two or more are blood chambers are alternatively stacked on one another chamber operably interact with each other for dialysis.

23. The dialysis device of claim 22, wherein the filtration unit further comprises at least one ultrafiltration membrane disposed between the at least one dialysis chamber and the at least one blood chamber such that the blood contained in the blood chamber is in contact with one surface of the at least one ultrafiltration membrane that face the blood chamber, the dialysate fluid contained in the at least one dialysis chamber is in contact with another surface of the at least one ultrafiltration membrane that face the at least one dialysis chamber.

24. The dialysis device of claim 23, wherein the filtration unit further comprises at least one diaphragm adapted to support the at least one ultrafiltration membrane, and formed of a flexible inert material that allows the at least one blood chamber to fill during expansion or to expel during contraction, while having opposite expansion or contraction effect on the at least one dialysis chamber.

25. The dialysis device of claim 23, wherein the at least one ultrafiltration membrane is a porous membrane having pores that permit molecules to travel between the at least one blood chamber and the at least one dialysis chamber, whereby substances in the blood to be removed from the blood are passable from the blood in the at least one blood chamber to the dialysate in the at least one dialysis chamber, or substances in the dialysate to be added into the blood are passable from the dialysate in the at least one dialysis chamber into the at least one blood chamber.

26. The dialysis device of claim 25, wherein the at least one ultrafiltration membrane is formed of electrospun fleece, or nanofibers of a polymer or a polymer composite material.

27. The dialysis device of claim 25, wherein the at least one ultrafiltration membrane is further adapted as a pressure barrier separating fluid volumes contained in the at least one dialysis chamber from that of the at least one blood chamber.

28. The dialysis device of claim 22, wherein the at least inlet of the at least one blood chamber is operably connected to a vascular system of the patient, the at least one inlet of the at least one dialysis chamber is operably connected to a dialysate reservoir, so that blood of the patient is flowable into and/or out of the at least one blood chamber, the dialysate in the dialysate reservoir is flowable into and/or out of the at least one dialysis chamber, whereby unwanted substances of the blood in the at least one blood chamber are exchangeable with the dialysate in the at least one dialysis chamber as the blood flows into and/or out of the at least one blood chamber.

29. The dialysis device of claim 22, wherein the at least inlet of the at least one blood chamber comprises an inlet and an outlet each having a valve configured such that when the at least one blood chamber fills with fresh or uncleansed blood, the valve of the inlet is opened, while the valve of the outlet is closed, and when the at least one blood chamber expels the purified blood, the valve of the outlet is opened, while the valve of the inlet is closed.

30. The dialysis device of claim 22, further comprising at least one pump coupled to the at least one dialysis chamber for conveying the dialysate to and/or from the at least one dialysis chamber.

31. The dialysis device of claim 30, wherein the at least one pump is further coupled to an internal dialysate reservoir and/or an external dialysate reservoir.

32. The dialysis device of claim 30, wherein the at least one pump is programmed to alternatively cause the at least one dialysis chamber to pump and expel the dialysate in a cycle of pre-determined periodicity, thereby causing the at least one blood chamber to alternately fill with and expel the blood for the dialysis.

* * * * *